(12) United States Patent
Kono et al.

(10) Patent No.: US 7,093,490 B2
(45) Date of Patent: Aug. 22, 2006

(54) ULTRASONIC FLAW DETECTING METHOD AND ULTRASONIC FLAW DETECTOR

(75) Inventors: Naoyuki Kono, Mito (JP); Tetsuya Matsui, Hitachi (JP); Masahiro Koike, Hitachi (JP); Masahiro Tooma, Kanasago (JP); Yoshinori Musha, Hitachiota (JP); Masahiro Miki, Tokai (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/049,949

(22) Filed: Feb. 4, 2005

(65) Prior Publication Data

US 2005/0183505 A1 Aug. 25, 2005

(30) Foreign Application Priority Data

Feb. 23, 2004 (JP) ............................. 2004-046583

(51) Int. Cl.
*G01N 9/24* (2006.01)

(52) U.S. Cl. .......................................... 73/602; 73/626

(58) Field of Classification Search ..................... None
See application file for complete search history.

(56) References Cited

U.S. PATENT DOCUMENTS

| 4,363,115 | A | * | 12/1982 | Cuomo | 367/154 |
| 4,543,828 | A | * | 10/1985 | Lerch | 73/626 |
| 4,648,080 | A | * | 3/1987 | Hargreaves | 367/20 |
| 4,870,623 | A | * | 9/1989 | Buckley et al. | 367/7 |
| 6,050,361 | A | * | 4/2000 | Ruffa et al. | 181/108 |
| 6,814,701 | B1 | * | 11/2004 | Tamura | 600/443 |
| 2005/0007882 | A1 | * | 1/2005 | Bachelor et al. | 367/103 |

FOREIGN PATENT DOCUMENTS

| JP | 11-328 | 6/1999 |
| JP | 2000-146921 | 5/2000 |
| JP | 2001-255308 | 9/2001 |

OTHER PUBLICATIONS

Handbook of Ultrasonic Diagnostic Equipment, Revised Edition, Electronic Industries of Japan (1997), pp. 39-40.
Ultrasonic Testing (Revised Edition), The 19th Committee on Steel-making Japan Society for Promotion of Science (1974), pp. 35-47 and 746.

* cited by examiner

*Primary Examiner*—Hezron Williams
*Assistant Examiner*—Rose M. Miller
(74) *Attorney, Agent, or Firm*—Mattingly, Stanger, Malur & Brundidge, P.C.

(57) ABSTRACT

In order to make it possible in ultrasonic flaw detection to generate ultrasonic waves containing a main beam only by use of an array probe and clearly identify a defect in a specimen by use of images, an element pitch P (the distance between centers of adjacent ultrasonic transducer elements in the array probe) is set longer than ¼ of the wavelength of longitudinal waves generated by the ultrasonic transducer elements and shorter than ½ of the wavelength and reception signals up to time corresponding to the sum of wall thickness round-trip propagation time for longitudinal waves and wall thickness round-trip propagation time for shear waves in the specimen are displayed.

6 Claims, 25 Drawing Sheets

| MATERIAL | V<br>VELOCITY FOR LONGITUDINAL WAVE | Vs<br>VELOCITY FOR SHEAR WAVE | V/Vs<br>WAVE VELOCITY RATIO |
|---|---|---|---|
| ALUMINUM | 6260 | 3080 | 2.03 |
| IRON | 5850 | 3230 | 1.81 |
| COPPER | 4700 | 2260 | 2.08 |
| NICKEL | 5630 | 2960 | 1.90 |
| QUARTZ GLASS | 5570 | 3515 | 1.58 |
| STAINLESS STEEL 302 | 5660 | 3120 | 1.81 |
| VINYL CHLORIDE | 2300 | 1100 | 2.09 |

\* VELOCITIES FOR LONGITUDINAL AND SHEAR WAVES ARE QUOTED FROM "ULTRASONIC TESTING (REVISED EDITION)"

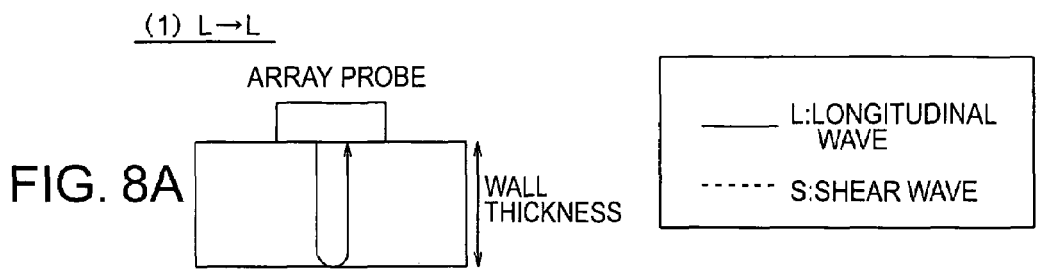
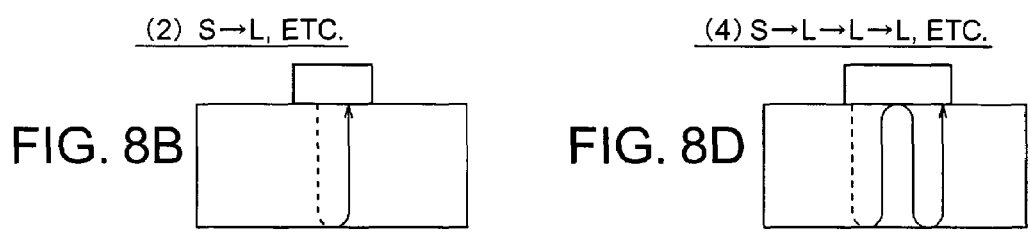
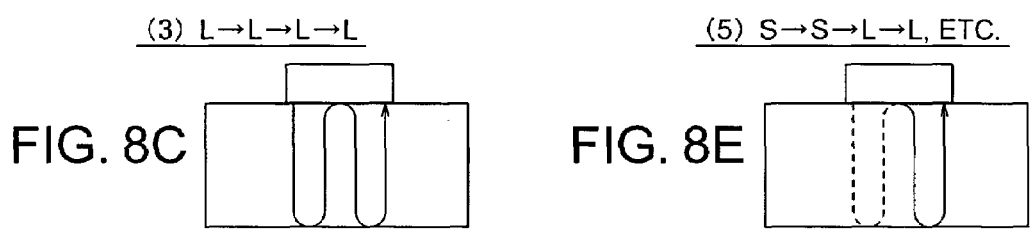
FIG. 8F
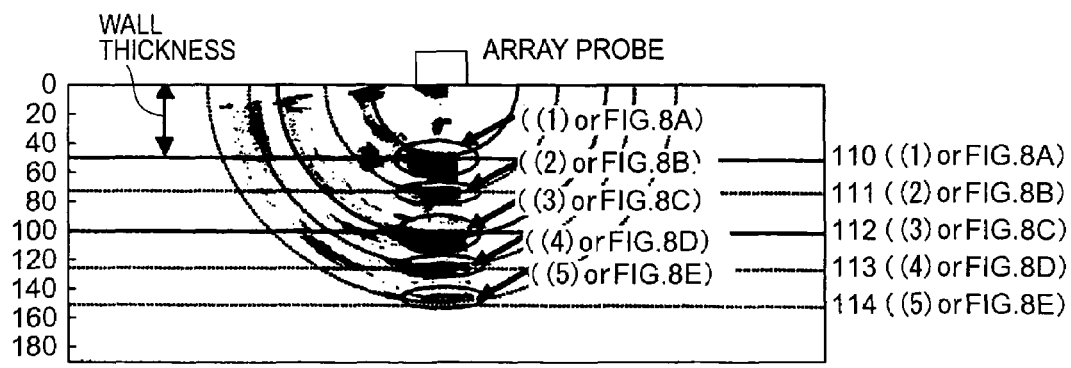

ULTRASONIC FLAW DETECTING METHOD AND ULTRASONIC FLAW DETECTOR

BACKGROUND OF THE INVENTION

The present invention relates to an ultrasonic flaw detection technique for inspecting a solid body, and in particular, to an ultrasonic flaw detection technique for carrying out ultrasonic flaw detection by a phased array technique by use of an array sensor.

As a nondestructive inspection technique for a solid body allowing propagation of both longitudinal waves and shear waves (e.g. steel), a technique using ultrasonic waves (ultrasonic flaw detection) has been generally used. As a type of the ultrasonic flaw detection, there exists flaw detection using the so-called phased array technique.

Here, the phased array technique is also called an "electronic scan technique", in which a probe including a plurality of ultrasonic generator elements (made of piezoelectric elements) arranged in an array (the so-called "array probe") is used. In the technique, electric signals as triggers for the generation of ultrasonic waves are successively supplied to the elements of the array probe at prescribed time intervals (delays) and the ultrasonic waves generated by the elements are superposed on one another to form a superposed wave, by which various conditions such as the transmission/reception angle/position of ultrasonic waves to/from the specimen being inspected, positions having enhanced energy due to the interference in the superposed wave (i.e. focal positions), etc. can be changed at high speed by means of electronic control.

The array probe is used for electrically scanning the flaw detection conditions since the transmission/reception angle/position and the focal positions of ultrasonic waves can be changed freely across a wide inspection range, by which an angle, position and focal points allowing reception of stronger reflected waves (echoes) from a reflector (defect, etc.) existing inside or on a surface of the specimen can be selected and thereby defects as reflectors can be found easily.

On the other hand, in a widely employed ultrasonic flaw detection technique using only one ultrasonic probe (two probes (transmission/reception probes) when separate probes are used for transmission and reception respectively), one probe can realize only one probe condition (transmission/reception angle, transmission/reception position, focal position), and thus a plurality of probes have to be prepared in order to achieve different flaw detection conditions.

Even the aforementioned phased array technique using an array probe is being adopted, in most cases, for the purpose of expanding the functions of conventional probes. Therefore, even when the integrity of a specimen is evaluated by use of the phased array technique, the so-called angled flaw detection technique (evaluating the integrity by letting shear waves or longitudinal waves propagate in the specimen in an oblique direction and receiving waves reflected by a reflector such as a defect) is mainly used, similarly to the case of flaw detection using a conventional probe.

The angled flaw detection technique can be characterized as having a common and fixed propagation mode (longitudinal or shear) of the wave transmitted, the wave propagating in the specimen and the wave received. For example, in an angled longitudinal wave flaw detection technique, a longitudinal wave transmitted is reflected by a reflector (defect, etc.) and the reflected wave is received by the probe also as a longitudinal wave.

Meanwhile, as a flaw detection technique using a fixed angle besides the angled flaw detection technique, there exist an ID creeping technique for judging whether there exists a reflector such as a defect and a mode conversion technique capable of roughly evaluating the dimensions of a defect.

These techniques can contribute to the improvement of reliability of the angled longitudinal wave technique. For example, when a defect existing in an inspection area of the specimen is searched for by use of an angled beam, there are cases where an echo (reflected wave) from a deformed part of the specimen (e.g. deformation caused by welding or machining) is received. In such cases, the discrimination between an echo caused by such a deformed part and an echo from a defect can be very difficult.

In such cases, if the aforementioned ID creeping waves or mode conversion waves are used together with the angled longitudinal waves (angled beam), discriminability of echoes can be increased and that contributes to the improvement of reliability of flaw detection results obtained by the angled flaw detection technique.

By the way, in the ID creeping waves and the mode conversion waves used in the aforementioned techniques, the wave transmitted, the wave propagating in the specimen and the wave received do not have the same propagation mode, differently from the case of the angled flaw detection technique. For example, in the ID creeping technique, shear ultrasonic waves (angle: approximately 30°), generated simultaneously with longitudinal waves (angle: approximately 70°) by a longitudinal wave probe, are used, and the propagation mode changes later as will be explained below.

Here, a brief outline of the propagation of ultrasonic waves in the ID creeping technique will be explained referring to FIG. 4. When a shear wave 401 is emitted from an ultrasonic transducer, the propagation mode of the wave changes from the shear wave to a longitudinal wave 402 (mode conversion) when the wave is reflected by a far surface (base) of the specimen. Thereafter, the longitudinal wave 402 is reflected by a crack corner of a crack (defect) 403. The crack corner of the crack is a portion near a surface of the specimen.

A longitudinal wave 404 (the longitudinal wave 402 after being reflected by the crack corner) propagates in the vicinity of the far surface of the specimen. During the propagation along the far surface, the longitudinal wave 404 converts into a shear wave 405 (mode conversion), by which the shear wave 405 returns to the ultrasonic transducer and is received as an echo from the crack corner.

As above, the ID creeping technique, enabling the reception of echoes from crack corners, is effective for judging whether a specimen has a defect or not.

In the so-called mode conversion technique using the mode conversion of ultrasonic waves as above, shear ultrasonic waves (angle: approximately 28°) generated simultaneously with longitudinal waves (angle: approximately 60°) by a longitudinal ultrasonic transducer are used.

Thus, a brief outline of the propagation of ultrasonic waves in the so-called mode conversion technique will be explained below referring to FIGS. 5A and 5B. The propagation mode of a shear wave 501 generated by an ultrasonic transducer changes from the shear wave to a longitudinal wave 502 when the wave is reflected by the far surface of the specimen.

In cases where a reflector 502 shown in FIG. 5A is a defect having a certain height, reflection occurs at the tip of the defect or on the surface of the defect on the way to the tip. A longitudinal wave 504 reflected by the defect returns directly to the ultrasonic transducer through the specimen and is received as an echo from the defect.

However, in the case of a reflector 507 shown in FIG. 5B which is relatively low, a longitudinal wave 506 (generated by the mode conversion from a shear wave 505 at the far surface of the specimen) can not meet the tip of the defect, by which there appears no ultrasonic wave returning to the ultrasonic transducer. As above, in the mode conversion technique, whether the defect has a certain height (approximately ⅓ of the wall thickness of the specimen) or not corresponds to the presence/absence of an echo from the defect. Thus, the mode conversion technique is effective for roughly determining the height of a defect.

However, since the two techniques explained above employ a judgment based on a waveform called "A-scan" (plotted on a graph with the vertical axis representing reception intensity of ultrasonic waves and the horizontal axis representing propagation distance or propagation time inside the specimen), it is extremely difficult and requires skill to clarify the origin of the complex propagation path inside the specimen shown in FIGS. 4, 5A and 5B and determine the presence/absence of a defect or the approximate size of the defect.

Meanwhile, in order to implement the aforementioned ID creeping technique or the mode conversion technique by use of an array probe, the array probe is required to generate both longitudinal waves and shear waves in intended directions.

However, with conventional array probes, the generation of longitudinal and shear waves in intended directions is generally accompanied by ultrasonic waves being radiated in other directions, by which the identification of propagation paths of received ultrasonic waves and the implementation of the above techniques by use of an array probe become difficult.

In the conventional phased array technique, two types of probes: an array probe making direct contact with the specimen for generating longitudinal waves (the so-called "array probe in contact technique") and an array probe supporting both longitudinal waves and shear waves using a wedge shaped intermediate medium called "wedge" or "shoe" (the so-called "array probe with a wedge") have been used mainly. Therefore, features and problems with each of the array probes will be explained below.

The array probe in contact technique is an array probe for longitudinal waves, placed to directly contact the specimen or to be in parallel with the specimen. In the array probe, ultrasonic transducer elements such as piezoelectric elements are arranged in a line (array) and the angle of transmission/reception of ultrasonic waves propagating in the specimen is electronically changed from vertical (angle: 0°) to 45° (or 60°).

In this case, longitudinal waves including components perpendicular to the specimen are generated by each ultrasonic transducer element of the array probe. Therefore, longitudinal waves propagating in an intended angle θ can be synthesized by giving a proper delay time determined by the following expression (1) to each element (see "Handbook of Ultrasonic Diagnostic Equipment (Revised Edition)", pp. 39–40, Electronic Industries Association of Japan (1997), for example):

$$\tau_i = (i-1) P \cdot \sin \theta / c \qquad (1)$$

where "i" denotes a serial number of each element, "$\tau_i$" denotes a delay time given to the i-th element, "c" denotes wave velocity (propagation speed) of longitudinal waves in the specimen (solid body), "P" denotes the element pitch, and "θ" denotes the incident angle (incident direction) of the ultrasonic waves.

It is well known that ultrasonic waves propagating in other directions φ are also synthesized in addition to the ultrasonic waves (main beam) propagating in the intended direction θ.

For preventing the synthesis of the undesired ultrasonic waves (hereinafter referred to as "grating lobes") other than the main beam propagating in the intended direction (angle) θ, the element pitch P in the expression (1) has to be set smaller than or equal to a value determined by the following expression (2):

$$P = \lambda / (1 + |\sin \theta|) \qquad (2)$$

where "λ" denotes the wavelength of longitudinal waves in the specimen (solid body).

Since the maximum value of the incident angle θ of the ultrasonic waves is 90°, the minimum value of the element gap in the expression (2) is ½ of the wavelength.

While the array probe in contact technique is capable of transmitting longitudinal waves in a wide range of angles without causing the grating lobes, a grating occurs to shear waves at the same time, hampering the implementation of the aforementioned ID creeping technique or mode conversion technique by use of the array probe.

There have been proposed a method and a device implementing an angled shear wave flaw detection technique by use of an array probe by focusing attention on shear waves simultaneously generated by the piezoelectric elements of the array probe, treating longitudinal waves generated simultaneously with the shear waves as noise, and reducing the noise (see JP-A-2001-255308, for example).

However, even the above proposition discloses nothing about an ID creeping technique or mode conversion technique that utilizes both longitudinal waves and shear waves simultaneously generated by the array probe.

Meanwhile, the array probe with a wedge is an array probe including an array sensor placed with a tilt angle relative to the specimen and an extra medium sandwiched between the array sensor and the specimen. Typical examples of the medium placed between the array sensor and the specimen include water and synthetic resin (acrylic, polystyrene, polyimide, etc.). The intermediate medium is called a "wedge" or "shoe" as mentioned above.

By use of the wedge, even when the incident angle of the ultrasonic waves upon the wedge is small, a large refractive angle for the incidence upon the specimen can be achieved thanks to the refraction of the ultrasonic waves (see "Ultrasonic Testing (Revised Edition)", pp. 35–47 and 746, The 19th Committee on Steelmaking, Japan Society for the Promotion of Science (1974), for example).

The following equation (3) represents the relationship between the incident angle θ' upon the wedge and the refractive angle θ into the specimen:

$$\theta' = \sin^{-1} \theta (\sin \theta \times V'/V) \qquad (3)$$

where "θ'" denotes the incident angle of the longitudinal waves upon the wedge, "θ" denotes the refractive angle of the ultrasonic waves incident upon the specimen, "V'" denotes wave velocity of longitudinal waves in the wedge, and "V" denotes wave velocity of longitudinal waves in the specimen (solid body).

For example, when ultrasonic waves are incident upon steel (iron) (wave velocity: approximately 5900 m/s (longitudinal wave), approximately 3000 m/s (shear wave)) from water (wave velocity: approximately 1500 m/s), shear waves incident upon the specimen at an incident angle of 70° can be achieved by letting the ultrasonic waves incident upon the water at an incident angle of approximately 14°. However, shear waves at an angle of approximately 29° develop in the steel at the same time.

By this, multiple reflection echoes inside the wedge are received by the probe as noise signals, which can hamper the identification of echoes from defects.

SUMMARY OF THE INVENTION

As described above, the aforementioned conventional techniques, having paid no attention to the generation of ultrasonic waves containing the main beam only and including no grating lobes (ultrasonic waves propagating in directions other than the intended direction) by use of an array probe, have difficulties in the implementation of the ID creeping technique and the mode conversion technique.

Further, the above conventional techniques have not focused on the identification of echoes (reflected waves) from defects and it has been difficult to clearly identify ID creeping waves or mode conversion waves by use of images.

It is therefore the primary object of the present invention to provide an ultrasonic flaw detection method and an ultrasonic flaw detector capable of generating ultrasonic waves containing the main beam only and including no grating lobes (ultrasonic waves propagating in directions other than the intended direction) in regard to both longitudinal waves and shear waves even when an array probe is used.

Another object of the present invention is to provide an ultrasonic flaw detection method and an ultrasonic flaw detector capable of realizing clear identification of defect echoes deriving from ID creeping waves or mode conversion waves propagating in the specimen through complex paths, by use of images. In the present invention, a wall of tube is also included in the specimen.

In order to achieve the above objects, in ultrasonic flaw detection according to the phased array technique using an array probe including an array of transducer elements, the distance between centers of adjacent transducer elements in the array probe is set longer than ¼ of the wavelength of longitudinal waves in a specimen as the object of flaw detection and shorter than ½ of the wavelength.

Preferably, reception signals obtained by the array probe are displayed for a period covering at least a time corresponding to the sum of round-trip propagation time for longitudinal waves in a wall thickness direction of the specimen and round-trip propagation time for shear waves in the wall thickness direction.

The integrity of the specimen may be evaluated based on the presence/absence of a signal displayed after time corresponding to twice the round-trip propagation time for longitudinal waves in the wall thickness direction and by time corresponding to the sum of the round-trip propagation time for longitudinal waves in the wall thickness direction and the round-trip propagation time for shear waves in the wall thickness direction. The integrity of the specimen may also evaluated based on the presence/absence of a signal displayed after time corresponding to the sum of one-way propagation time for longitudinal waves in the wall thickness direction of the specimen (100) and one-way propagation time for shear waves in the wall thickness direction and by time corresponding to the sum of three times the one-way propagation time for longitudinal waves in the wall thickness direction and the one-way propagation time for shear waves in the wall thickness direction.

By use of an array probe in which the distance between centers of adjacent transducer elements is set between ¼ wavelength and ½ wavelength of longitudinal waves generated by the transducer elements as above, ultrasonic waves containing the main beam only and including no grating lobes (ultrasonic waves propagating in directions other than the intended direction) can be generated in regard to both longitudinal waves and shear waves even by use of an array probe.

In this case, the reception signals up to the time corresponding to the sum of the wall thickness round-trip propagation time for longitudinal waves and the wall thickness round-trip propagation time for shear waves in the specimen are displayed, and based on the presence/absence of a signal displayed after time corresponding to twice the wall thickness round-trip propagation time for longitudinal waves and by time corresponding to the sum of the wall thickness round-trip propagation time for longitudinal waves and the wall thickness round-trip propagation time for shear waves, the presence/absence of an echo from a defect deriving from the ID creeping waves can be judged and whether the specimen has a defect or not can be judged based on images.

Further, based on the presence/absence of a signal displayed after time corresponding to the sum of the wall thickness one-way propagation time for longitudinal waves and the wall thickness one-way propagation time for shear waves and by time corresponding to twice the wall thickness round-trip propagation time for longitudinal waves, the presence/absence of an echo from a defect deriving from the mode conversion waves can be judged and the approximate height of the defect can be evaluated based on images.

By the present invention, in a specimen including a solid body allowing propagation of both longitudinal waves and shear waves, ultrasonic waves containing the main beam only and including no grating lobes (ultrasonic waves propagating in directions other than the intended direction) can be generated in regard to both longitudinal waves and shear waves by use of an array probe.

Further, also regarding ID creeping waves and mode conversion waves having complex propagation paths, the presence/absence of signals displayed in particular areas specified by particular propagation times is judged, by which defect echoes deriving from the ID creeping waves and mode conversion waves can be identified clearly based on images. By this, the presence/absence of a defect in the specimen can be judged reliably and the approximate height of the defect can be evaluated.

BRIEF DESCRIPTION OF THE DRAWINGS

The objects and features of the present invention will become more apparent from the consideration of the following detailed description taken in conjunction with the accompanying drawings, in which:

FIGS. 8A–8F are schematic diagrams showing multiple reflection bottom echoes in a specimen and a display image;

DESCRIPTION OF THE EMBODIMENTS

Figure 1:
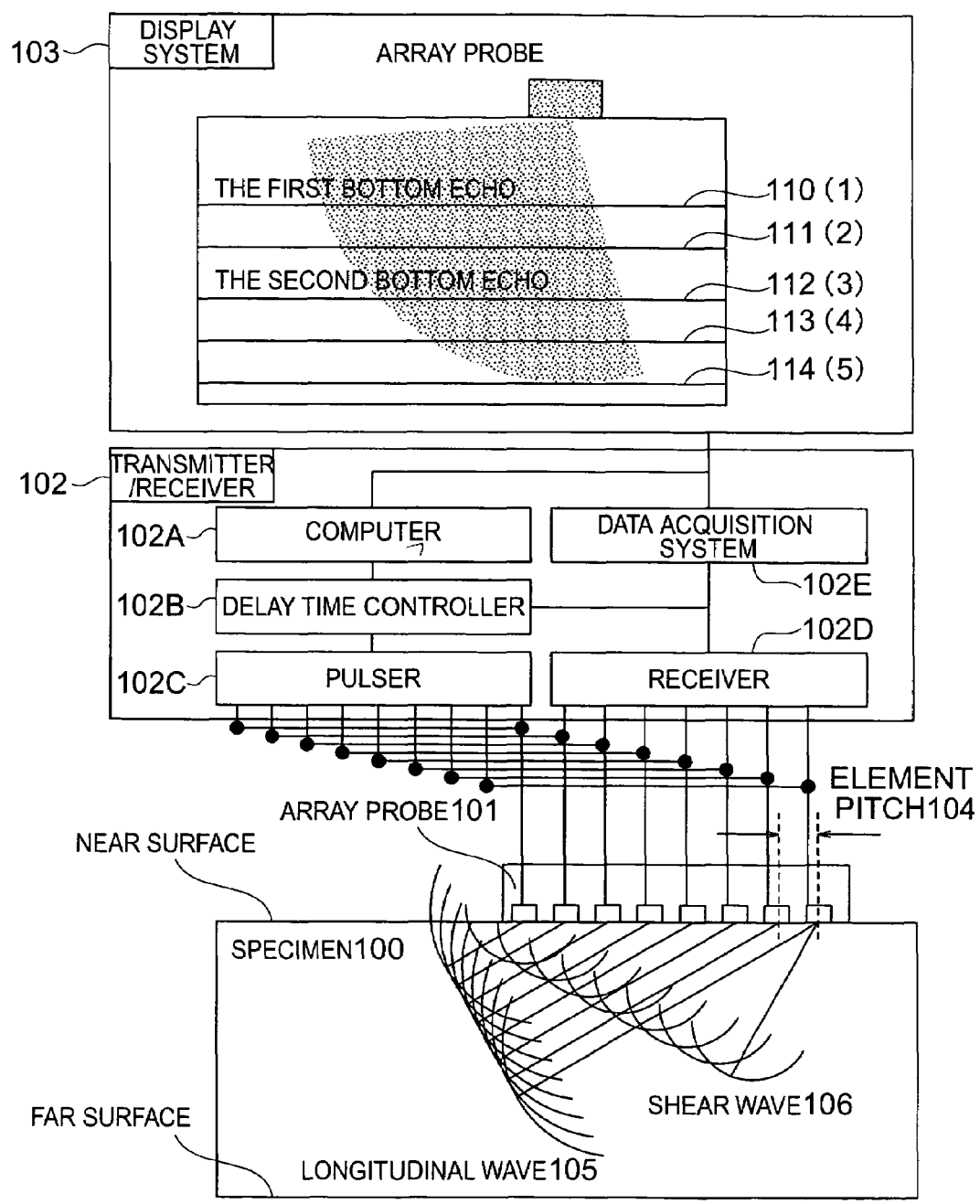
FIG. 1 is a schematic diagram for explaining an ultrasonic flaw detection method and an ultrasonic flaw detector in accordance with a first embodiment of the present invention.

Referring now to the drawings, a description will be given in detail of embodiments in accordance with the present invention. In each drawing, the specimen illustrated by a box also represents a sectional plane in an axial direction of a tube shaped specimen as well as that of plate shaped specimen.

Embodiment 1

FIG. 1 is a schematic diagram for explaining an ultrasonic flaw detection method and an ultrasonic flaw detector in accordance with a first embodiment of the present invention. The embodiment shown in FIG. 1 includes a specimen 100 as the object of inspection, an array probe 101 which emits ultrasonic waves into the specimen 100, a transmitter/receiver 102, and a display system 103 which displays received signals. Incidentally, in the first embodiment, an example of flaw detection in search of a defect (crack) open to the far surface of the specimen 100 will be explained.

The array probe 101 is set on a flaw detection surface (near surface) of the specimen 100 to generate ultrasonic waves in response to a driving signal supplied from the transmitter/receiver 102. The ultrasonic waves emitted by the array probe 101 propagates through the specimen 100, and reflected waves are detected by the array probe 101. A reception signal generated by the array probe 101 according to the detection of the reflected waves (echoes) is inputted to the transmitter/receiver 102.

The transmitter/receiver 102 includes a computer 102A, a delay time controller 102B, a pulser 102C, a receiver 102D and a data acquisition system 102E. The driving signal is supplied from the pulser 102C to the array probe 101, while the reception signal outputted by the array probe 101 accordingly is processed by the receiver 102D.

The computer 102A controls the delay time controller 102B, the pulser 102C, the receiver 102D and the data acquisition system 102E so that the components will operate properly.

The delay time controller 102B controls the timing of the driving signal outputted by the pulser 102C while controlling input timing of the reception signal by the receiver 102D so as to achieve the operation of the array probe 101 according to the phased array technique.

The data acquisition system 102E processes the reception signal supplied from the receiver 102D and supplies the result of the processing to the display system 103. The operation of the display system 103 will be described in detail later.

Figure 2:
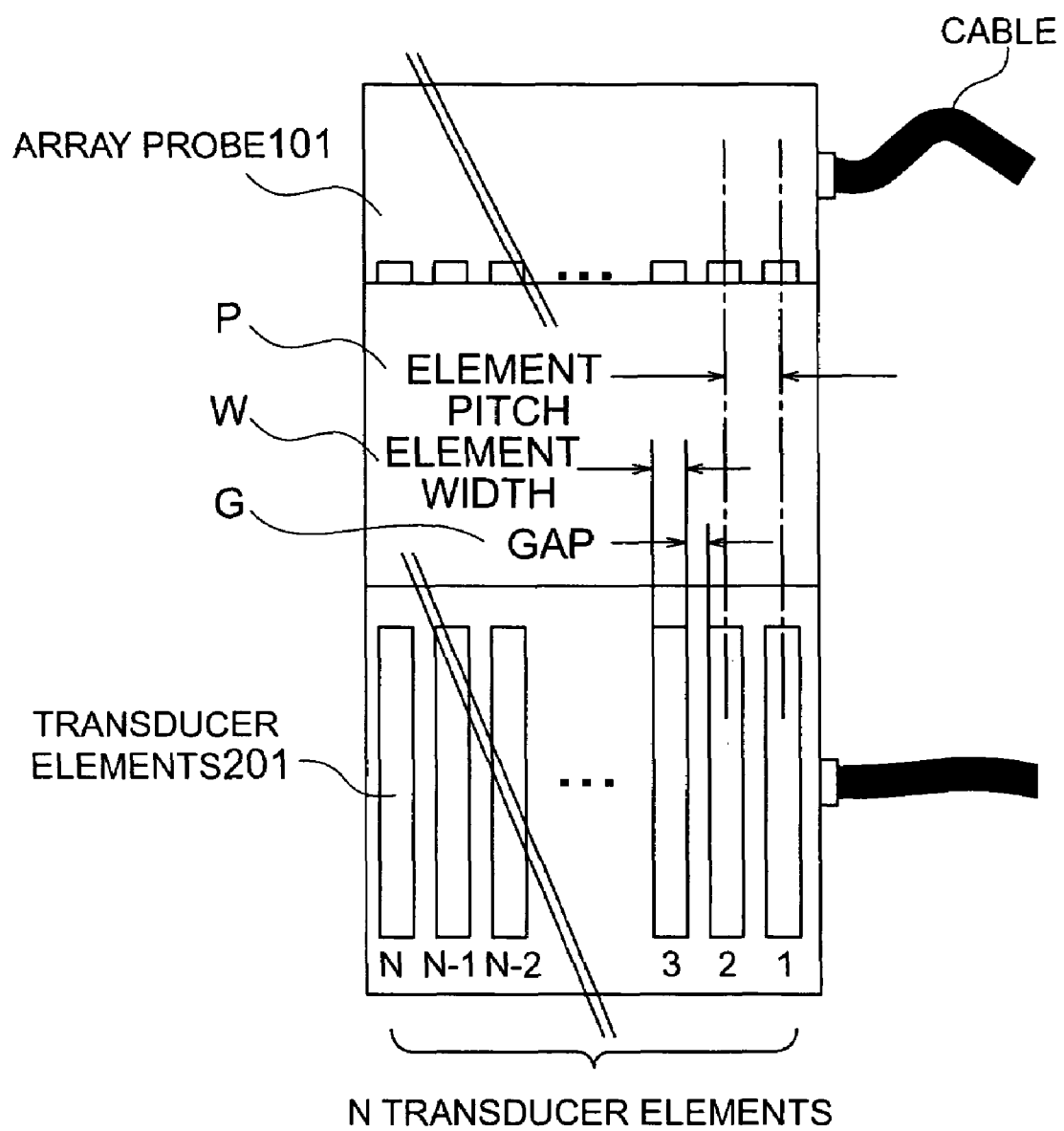
FIG. 2 is a schematic diagram showing an example of the composition of an array probe (ultrasonic transducer) employed in the first embodiment of the present invention.

Next, the details of the array probe 101 will be explained referring to FIG. 2. FIG. 2 is a schematic diagram showing the most basic composition of the array probe 101. As shown in FIG. 2, the array probe 101 is basically composed of a plurality of ultrasonic transducer elements 201.

In this embodiment, a composite piezoelectric body (also called a "composite") including a thin bar of PZT piezoelectric ceramic embedded in a polymeric material is used as an example of the ultrasonic transducer element 201. In this case, parameters determining the performance of the array probe 101 include an element pitch P.

The element pitch P is a length obtained by adding an element width W of the ultrasonic transducer element 201 to a gap G between the elements. The element pitch P is one of the major factors determining the generation of the main beam and grating lobes by the array probe 101.

As explained in the description of background arts, the conventional techniques have aimed at the generation of longitudinal waves and thus ultrasonic transducer elements for generating the longitudinal waves have been designed focusing mainly on the longitudinal waves which are formed by the superposition of ultrasonic waves generated by the elements. Therefore, in order to prevent the generation of grating lobes (ultrasonic waves propagating in directions other than the intended incident direction) regarding the longitudinal waves, the element pitch has generally been set to ½ of the wavelength.

Here, effects of the element pitch will be explained referring to FIGS. 3A, 3B and 3C. First, calculations for an array probe including 24 elements generating ultrasonic waves including longitudinal waves propagating in an angle of 60° in steel will be shown.

Figure 3A:
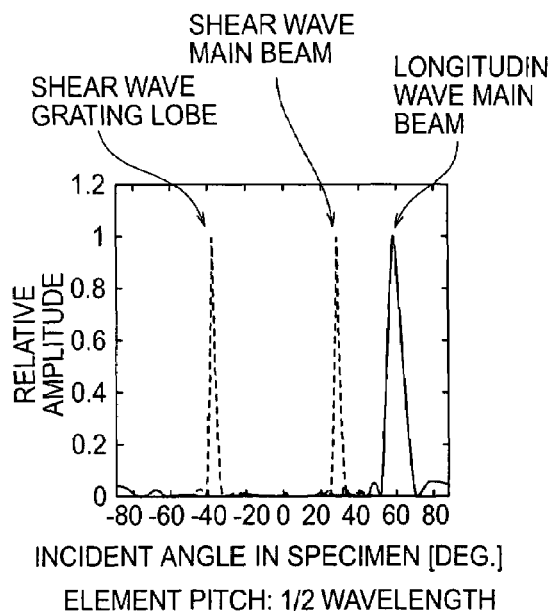
FIGS. 3A–3C are graphs for explaining a main beam and a grating lobe of longitudinal/shear waves generated by the ultrasonic transducer.

FIG. 3A shows the main beam and grating lobes obtained by setting the element pitch to ½ of the wavelength as in the conventional array probes. FIG. 3B shows a case where the element pitch is reduced to ¼ of the wavelength. FIG. 3C shows a case where an element pitch proposed by the present invention (⅓ of the wavelength) is employed.

As seen in the figures, the conventional element pitch (½ wavelength) and the element pitch of the present invention (⅓ wavelength) both cause a main beam (longitudinal waves) in the intended direction 60° and there is no problem about this point.

However, if we focus attention on shear waves generated simultaneously with the longitudinal waves, although the shear waves should include only a main beam propagating in a direction of approximately 29°, other shear waves (grating lobe) developing in approximately −40° is seen in FIG. 3A employing the conventional element pitch.

Figure 3B:
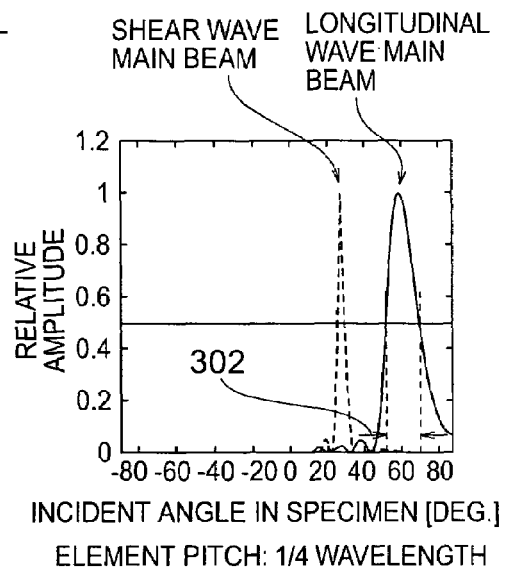
Figure 3C:
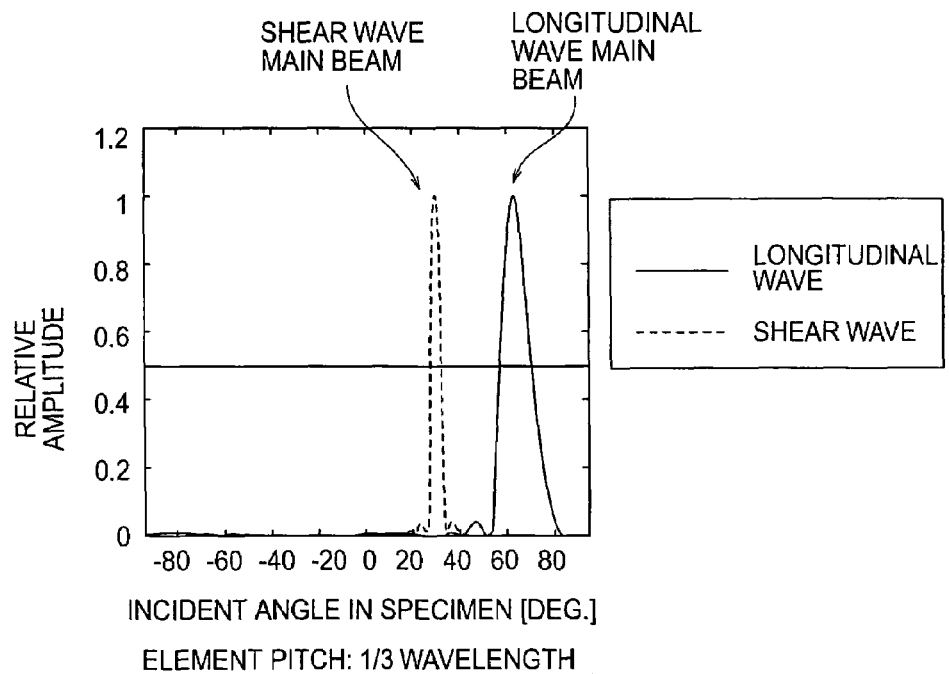

Meanwhile, in the case of FIG. 3C employing the element pitch of the present invention (⅓ wavelength), even the shear waves generated by the array probe include the main beam only, showing that the element pitch of the present invention also satisfies the condition regarding the shear waves.

The case of FIG. 3B where the element pitch is further reduced from ⅓ wavelength seems to have no particular problem since no grating lobe develops both in the longitudinal waves and shear waves. However, if we pay attention to the longitudinal waves, the half value width of the main beam propagating in the direction of 60° (hereinafter referred to as a "directivity angle") in FIG. 3B has become wider (approximately 20°) than that in FIG. 3C. By the broadening of the directivity angle, the identification of the directions of received signals (echoes from reflectors) becomes difficult.

Thus, in order to implement the ID creeping technique or mode conversion technique generating both longitudinal ultrasonic waves and shear ultrasonic waves by use of an array probe, it is necessary to generate the main beam only in regard to both the longitudinal waves and the shear waves while keeping the directivity angle within a certain range so that the directions of echoes received from the reflectors can be identified.

For the above reasons, the present invention employs a condition causing no grating lobe inside a shear wave angle range (shear wave critical angle) when the longitudinal waves propagate in the 90-degree direction (see equation (4)) as a standard for determining the element pitch.

$$d = \frac{\lambda}{1 + (V/Vs)} \quad (4)$$

where "λ" denotes the wavelength of longitudinal waves in the specimen, "V" denotes the wave velocity of longitudinal waves in the specimen and "Vs" denotes the wave velocity of shear waves in the specimen.

Figures 6, 7:
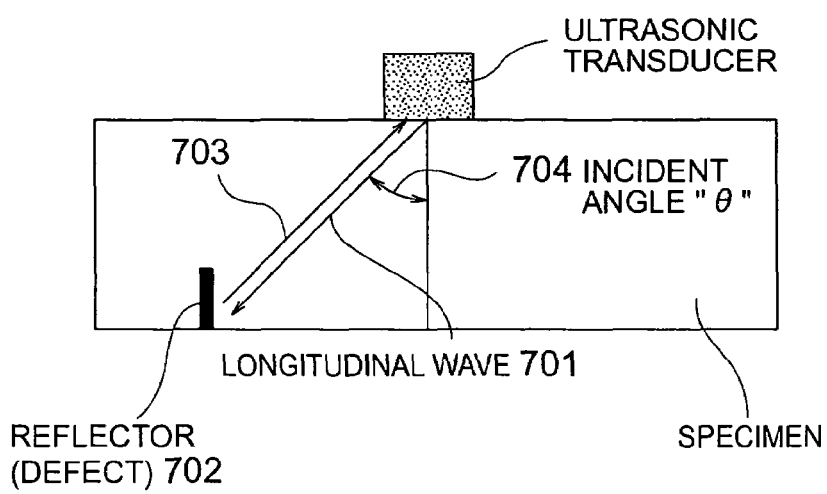
FIG. 6 is a table for explaining longitudinal/shear wave velocities and wave velocity ratios in various solid bodies.
FIG. 7 is a schematic diagram for explaining an angled flaw detection technique.

The ratio between longitudinal wave velocity V and shear wave velocity Vs in a solid body (V/Vs: wave velocity ratio) takes on values around 2 in many solid bodies as shown in FIG. 6 (see "Ultrasonic Testing (Revised Edition)," The 19th Committee on Steelmaking, Japan Society for the Promotion of Science (1974)).

Therefore, by generalizing the result of the equation (4), the present invention regards the optimum element pitch to be around ⅓ wavelength of the longitudinal waves (from ¼ wavelength to ½ wavelength).

For example, when the longitudinal wave velocity in the specimen is 6000 m/s and the frequency of the ultrasonic waves used in this case is 2 MHz, an element pitch 1.0 mm (⅓ wavelength) may be selected as the optimum element pitch in the embodiment of the present invention.

In this case, by adopting an element width W=0.9 mm and a gap G=0.1 mm, for example, longitudinal ultrasonic waves and shear ultrasonic waves with no grating lobes can be transmitted and received.

Next, a method for displaying the flaw detection results in accordance with an embodiment of the present invention will be described below. The ID creeping waves and the mode conversion waves are characterized by shear waves which propagate in the specimen at lower wave velocity than longitudinal waves.

Thus, the ID creeping waves and the mode conversion waves need more propagation time until the reflected waves are received by the probe, in comparison with the ordinary angled longitudinal wave flaw detection technique which deals with the propagation of longitudinal waves only.

FIG. 7 shows a brief outline of the propagation path of longitudinal waves in a 45-degree angled longitudinal wave technique (transmitting and receiving longitudinal waves at an angle of 45°) which is widely employed in the angled longitudinal wave technique. In this case, a longitudinal wave 701 transmitted by the ultrasonic transducer reaches a reflector 702, gets reflected by the corner or the tip of the reflector, returns to the ultrasonic transducer as a longitudinal wave 703, and is received by the ultrasonic transducer as a signal.

Figure 4:
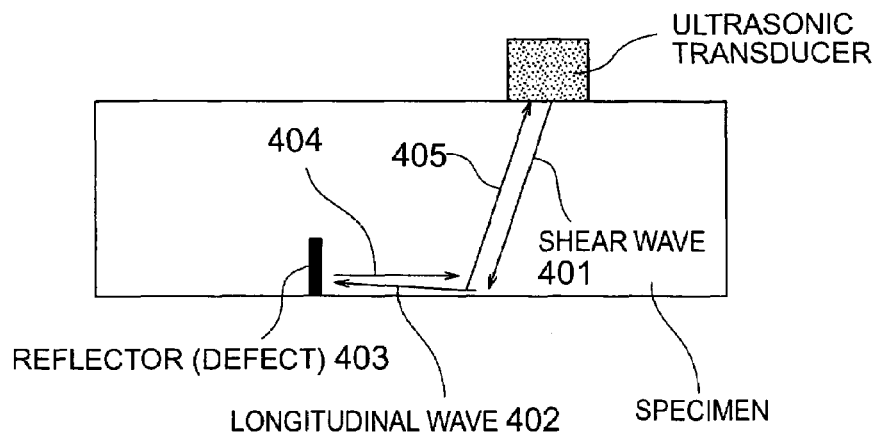
FIG. 4 is a schematic diagram for explaining an ID creeping technique.
Figure 5A:
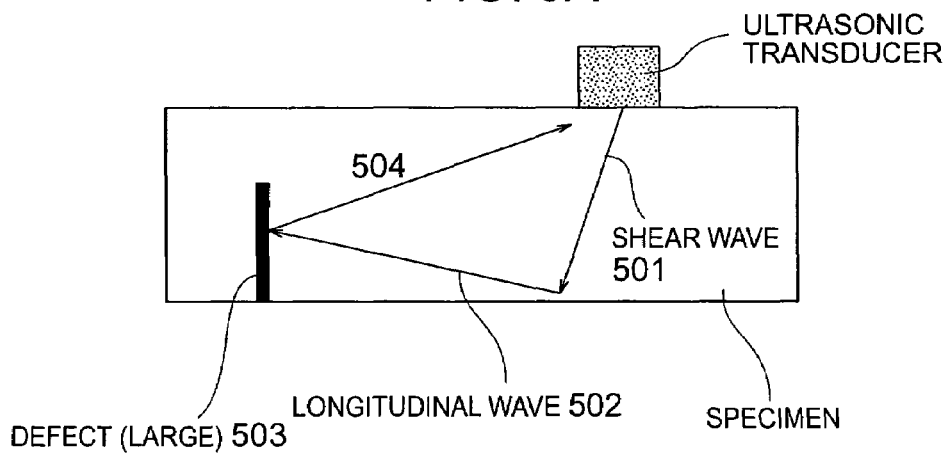
FIGS. 5A and 5B are schematic diagrams for explaining a mode conversion technique.
Figure 5B:
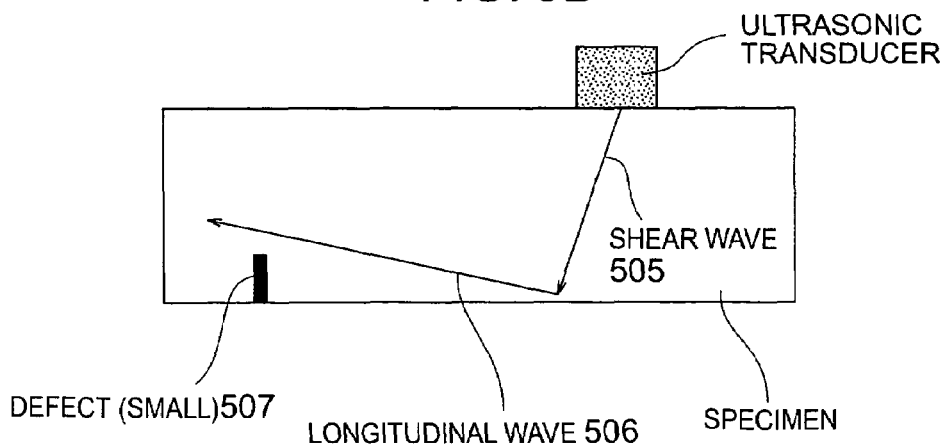

Compared with the 45-degree angled longitudinal wave technique shown in FIG. 7, the propagation path in the ID creeping technique or the mode conversion technique of the present invention is more complex and longer as explained referring to FIGS. 4, 5A and 5B. Therefore, in order to display the reflected waves (echoes) properly, it is necessary to keep on displaying the echoes during a proper time period corresponding to a certain propagation time.

Therefore, in this embodiment, time lengths regarding multiple bottom echoes developing in the specimen are used as standards for determining the propagation time for the waveform display. FIGS. 8A–8F are schematic diagrams showing examples of visualization of multiple bottom echoes in a tabular specimen by use of a phased array technique (electronically scanning the incident angle of ultrasonic waves) and propagation paths in the multiple reflections.

With an array probe set on a near surface of the specimen, multiple reflection is caused between the near surface and far surface of the specimen. FIGS. 8A–8E summarize types of echoes included in the multiple reflection in ascending order of propagation time. Multiple bottom echoes deriving from the five events are actually received by the array probe as shown in FIG. 8F which represents an example of a resultant image of the flaw detection by use of the array probe (see black parts in ellipses (1)–(5) in FIG. 8F). FIGS. 8A–8E correspond to (1)–(5), respectively.

Therefore, in the embodiment of the present invention, identifiability of the ID creeping waves and mode conversion waves is increased by considering the following five time lengths.

i. time of a first bottom echo corresponding to wall thickness round-trip propagation time for longitudinal waves (FIG. 8A)

ii. time corresponding to the sum of wall thickness one-way propagation time for longitudinal waves and wall thickness one-way propagation time for shear waves (FIG. 8B)

iii. time of a second bottom echo corresponding to twice the wall thickness round-trip propagation time for longitudinal waves (FIG. 8C)

iv. time corresponding to the sum of three times the wall thickness one-way propagation time for longitudinal waves and the wall thickness one-way propagation time for shear waves (FIG. 8D)

v. time corresponding to the sum of wall thickness round-trip propagation time for longitudinal waves and wall thickness round-trip propagation time for shear waves (FIG. 8E).

Here, the line 110 shown in the display system 103 in FIG. 1 represents the time corresponding to the round-trip propagation time for longitudinal waves (first bottom echo) (corresponding to FIG. 8A or (1)). In other words, the line 110 represents the far surface of the specimen. Similarly, the line 111 represents the time corresponding to FIG. 8B or (2), the line 112 represents the time corresponding to FIG. 8C or (3), the line 113 represents the time corresponding to FIG. 8D or (4), and the line 114 represents the time corresponding to FIG. 8E or (5).

As a display method for displaying the results in accordance with the present invention, lines corresponding to the time lengths of the multiple bottom echoes (or distances obtained by multiplying the time lengths by the wave velocity) like those shown in FIG. 1 or concentric circles corresponding to the time lengths of the multiple echoes (or distances obtained by multiplying the time lengths by the wave velocity) like those shown in FIGS. 8F may be displayed. It is also possible to combine the two display methods.

Next, a concrete example of a waveform identification method in accordance with an embodiment of the present invention will be explained in detail referring to FIGS. 9A and 9B. In this example, the ultrasonic flaw detection is assumed to be carried out for a specimen having a crack (defect) open to its far surface. When an echo that seems to be indicating a defect (hereinafter referred to as an "indication") is obtained, whether there exists a defect or not is judged for areas shown in FIG. 9A according to the flow chart of FIG. 9B.

Figure 9A:
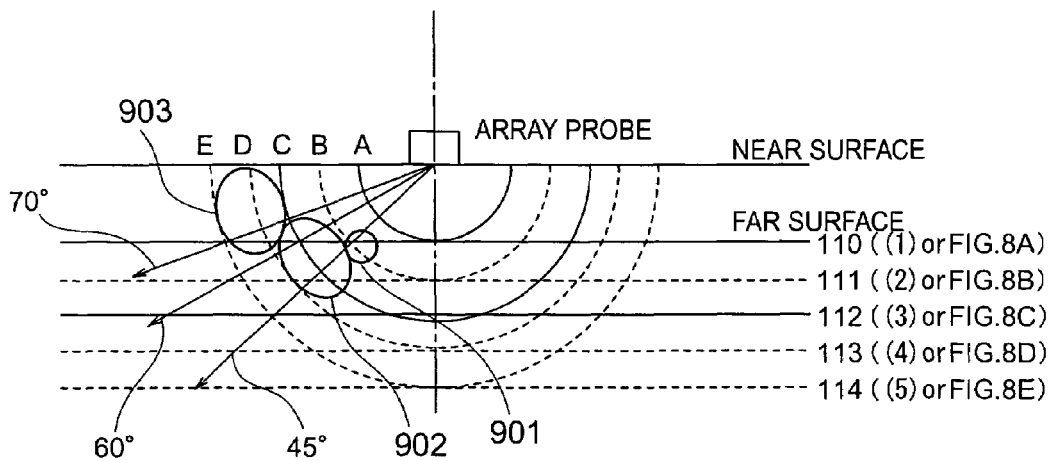
FIG. 9A is a schematic diagram showing a display method employed in the first embodiment of the present invention.
Figure 9B:
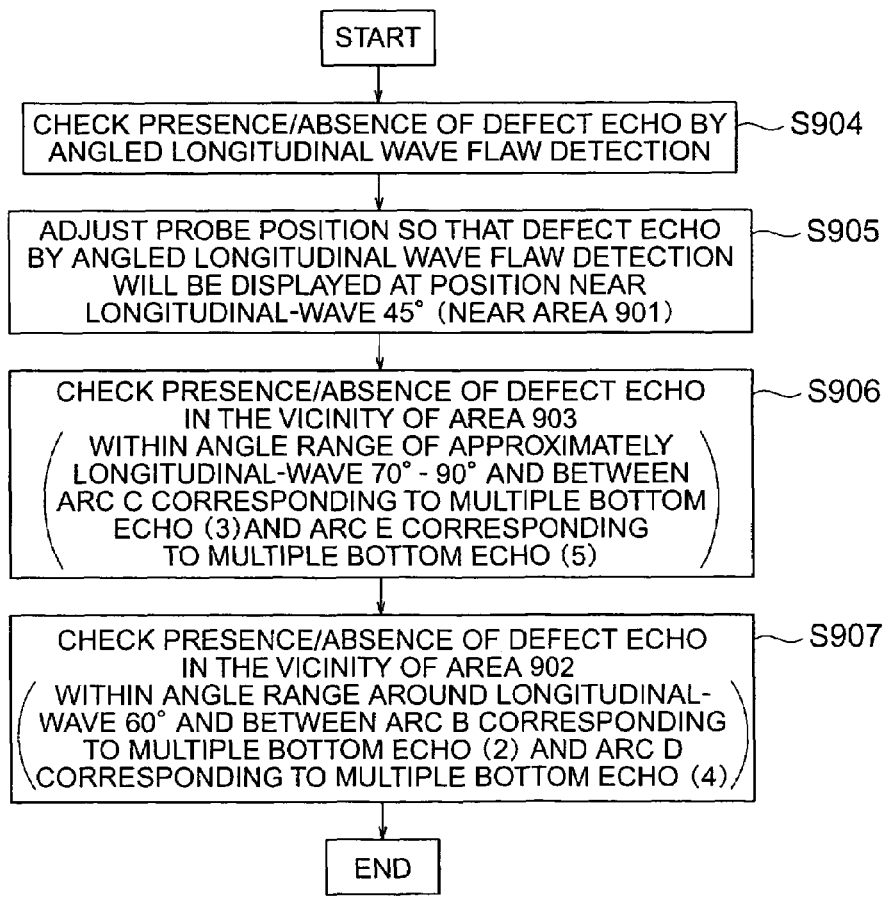
FIG. 9B is a flow chart showing a display method employed in the first embodiment of the present invention.

First, the presence/absence of an indication is checked by an ordinary angled flaw detection technique (S904), and the angle of the angled longitudinal wave technique is set to approximately 45°, or the position of the ultrasonic transducer (probe) is adjusted so that an indication by the angled longitudinal wave technique will be displayed in the vicinity of an area 901 shown in FIG. 9A (S905).

Subsequently, the presence/absence of an echo in an area 903 is checked in order to determine the presence/absence of an echo caused by an ID creeping wave (S906). Finally, the presence/absence of an echo in an area 902 is checked in order to determine the presence/absence of an echo caused by a mode conversion wave (S907).

When a signal is found in the step S904, S906 or S907, the indication is regarded to be one that might have been caused by a defect.

Here, before explaining a concrete example of flaw detection by use of the indications, characteristics of each area where a signal appears in each step of FIG. 9B (i.e. the areas 901, 902 and 903 in FIGS. 9A and 9B) will be explained in detail.

<Area 901>

The propagation distance of a 45-degree echo is obtained by multiplying the depth of the far surface by 1/cos 45°. Meanwhile, propagation time of the multiple echo (1) is approximately 1.5 times that corresponding to the far surface since the ratio V/Vs between the longitudinal wave velocity V and the shear wave velocity Vs in a solid body is approximately 2 as shown in FIG. 6.

Since the two propagation times are approximately the same, the reflected wave received at approximately 45° (longitudinal wave) is displayed in the vicinity of the area 901 (where an arc B corresponding to the propagation time of the multiple echo (2) intersects with the 45-degree line).

<Area 903>

In the judgment on the presence/absence of a defect by use of ID creeping waves, the array probe for the angled longitudinal wave flaw detection is assumed to be set at a position where the angle θ shown in FIG. 7 is approximately 45°.

Figure 10:
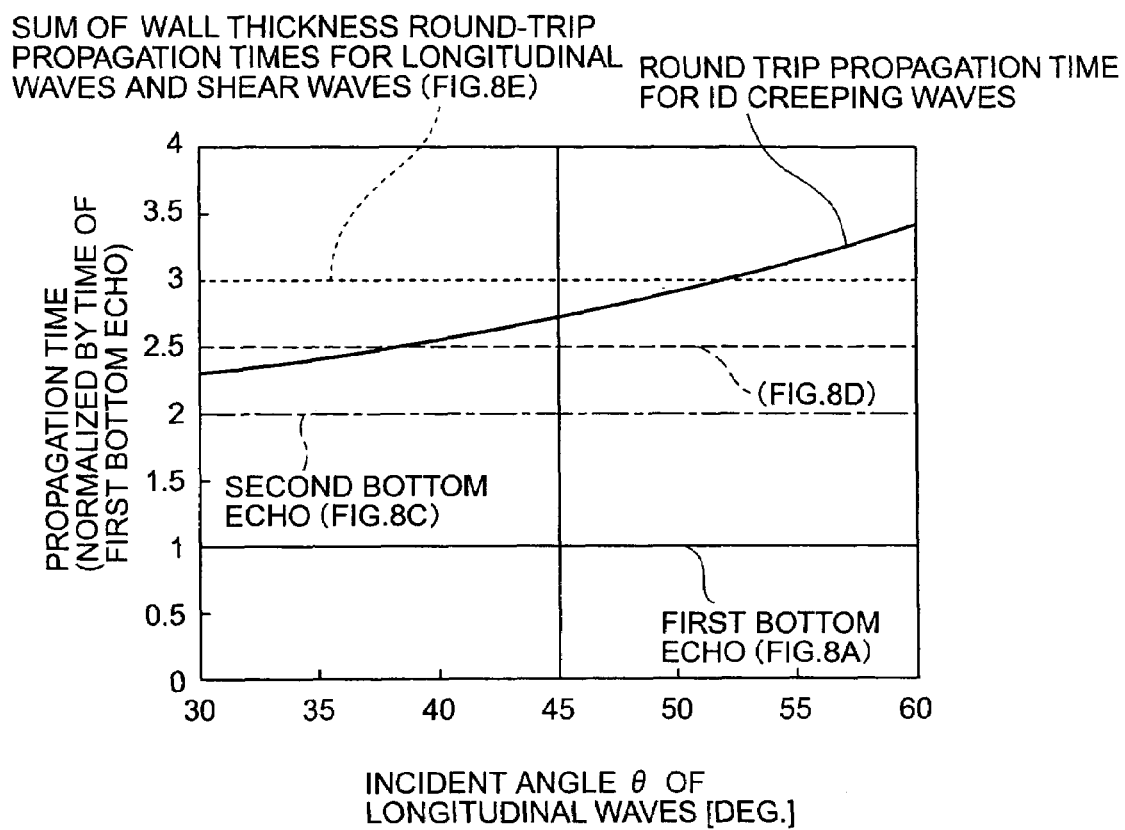
FIG. 10 is a graph explaining propagation times of echoes caused by ID creeping waves employed in the first embodiment of the present invention.
Figure 11:
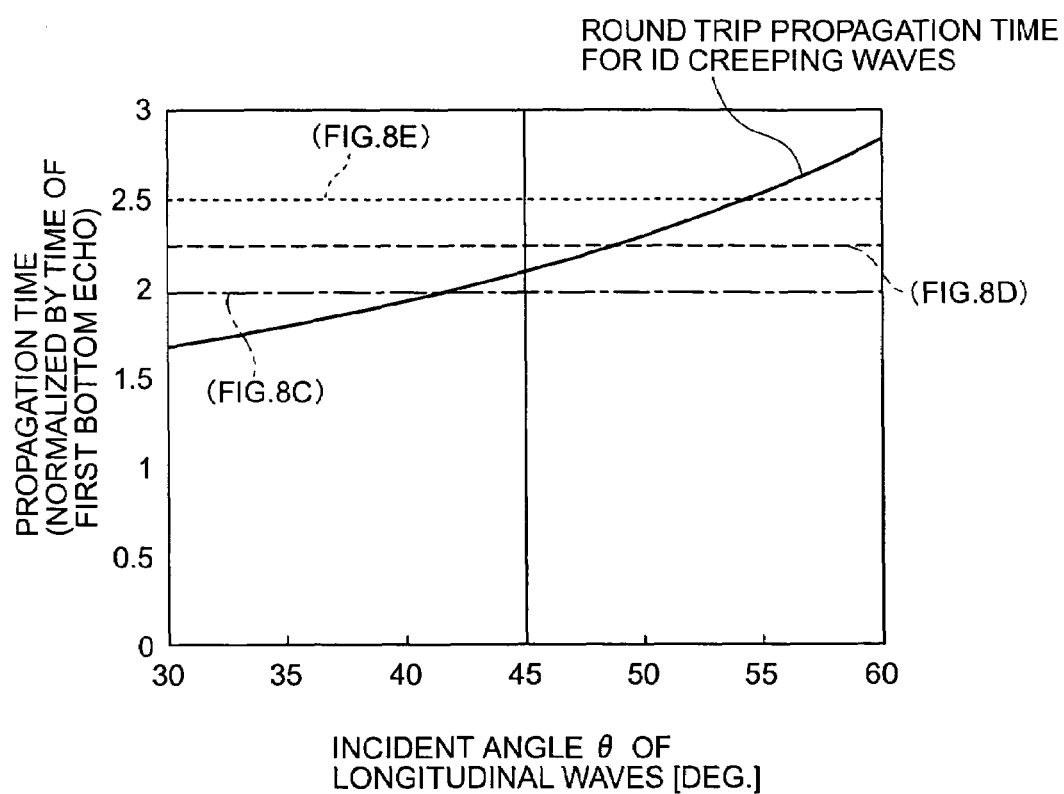
FIG. 11 is a graph explaining propagation times of echoes caused by ID creeping waves employed in the first embodiment of the present invention.
Figure 12:
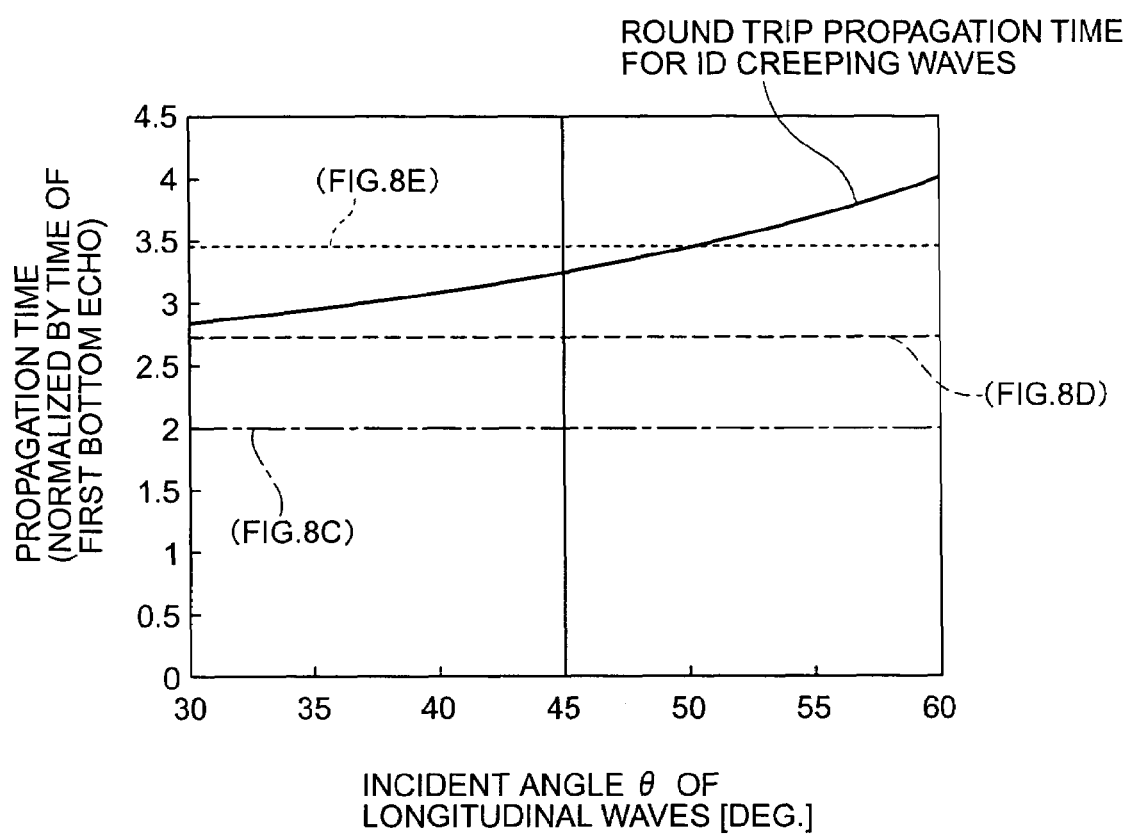
FIG. 12 is a graph explaining propagation times of echoes caused by ID creeping waves employed in the first embodiment of the present invention.

FIGS. 10, 11 and 12 are graphs comparing the total round-trip propagation time for ID creeping waves along the paths 401, 402, 404 and 405 shown in FIG. 4 with round-trip propagation times for multiple bottom echoes, in which FIGS. 10, 11 and 12 represent cases where the wave velocity ratio V/Vs is 2, 1.5, and 2.5, respectively. In the graphs, the longitudinal wave velocity V is fixed at 5900 m/s and the shear wave velocity Vs is changed depending on the wave velocity ratio V/Vs.

As is also clear from the graphs of FIGS. 10, 11 and 12, in ordinary solid bodies having wave velocity ratios V/Vs within a range of 2±0.5, the round-trip propagation time for the ID creeping waves stays between the time corresponding to the sum of the wall thickness round-trip propagation time for longitudinal waves and the wall thickness round-trip propagation time for shear waves (FIG. 8E) and the time corresponding to twice the wall thickness round-trip propagation time for longitudinal waves (FIG. 8C) even if the flaw detection angle θ of the angled longitudinal wave technique deviates from 45° by approximately 5°.

Therefore, echoes caused by the ID creeping waves are displayed in the area 903 (which is surrounded by the two propagation times (FIG. 8C and FIG. 8E) and boundaries of the flaw detection angle (70° and 90°) for the ID creeping waves), and whether a defect exists or not can be judged based on the presence/absence of a signal in the area.

<Area 902>

In the judgment on the presence/absence of a defect by use of mode conversion waves, the array probe for the angled longitudinal wave flaw detection is assumed to be set at a position where the angle θ shown in FIG. 7 is approximately 45°.

Figure 13:
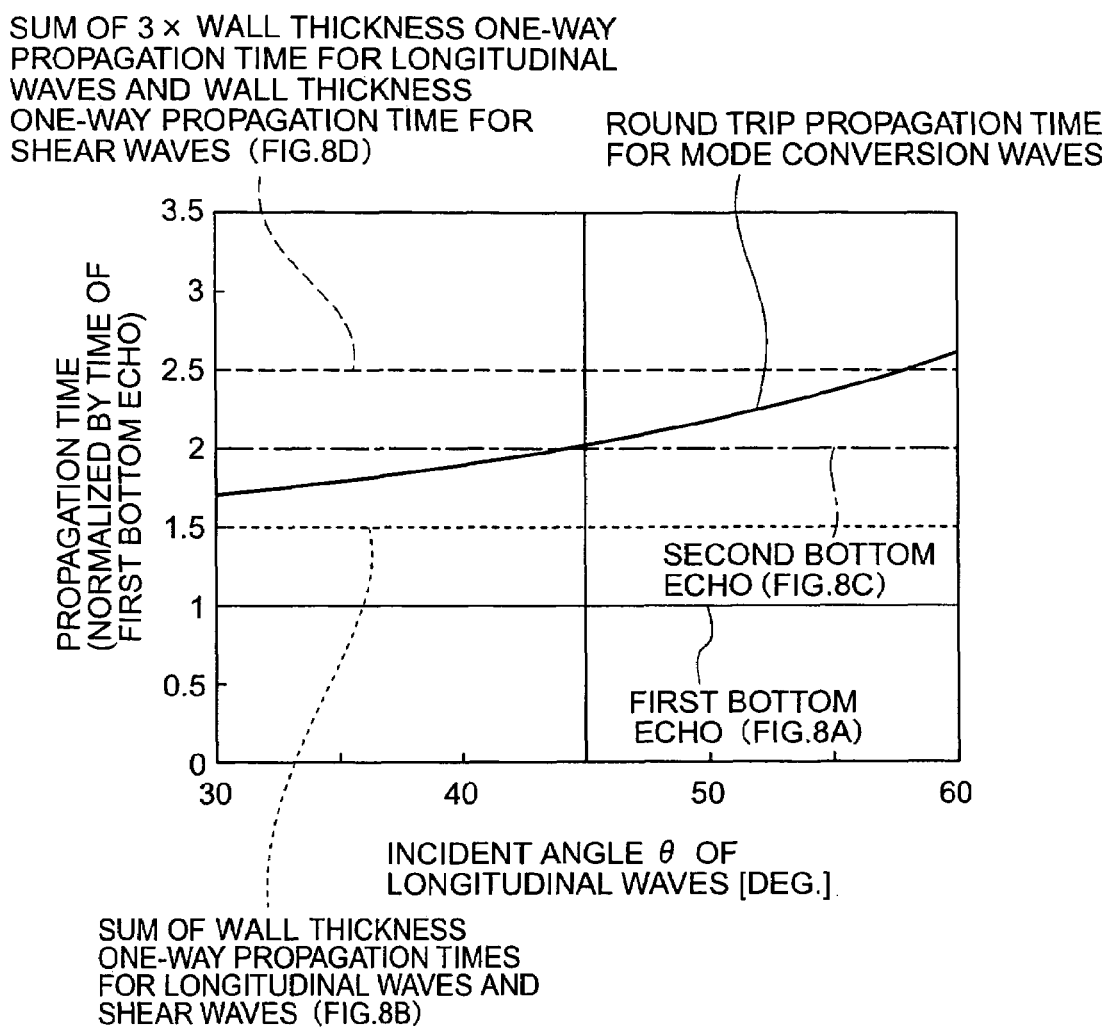
FIG. 13 is a graph explaining propagation times of echoes caused by mode conversion waves employed in the first embodiment of the present invention.
Figure 14:
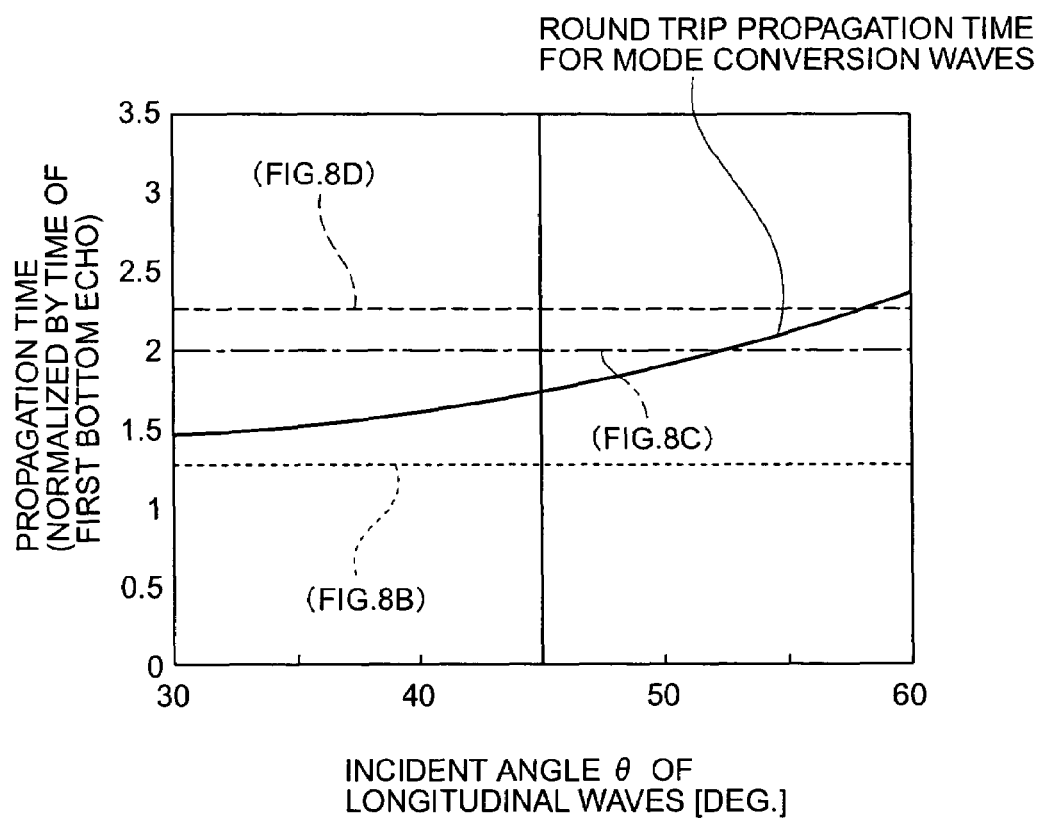
FIG. 14 is a graph explaining propagation times of echoes caused by mode conversion waves employed in the first embodiment of the present invention.
Figure 15:
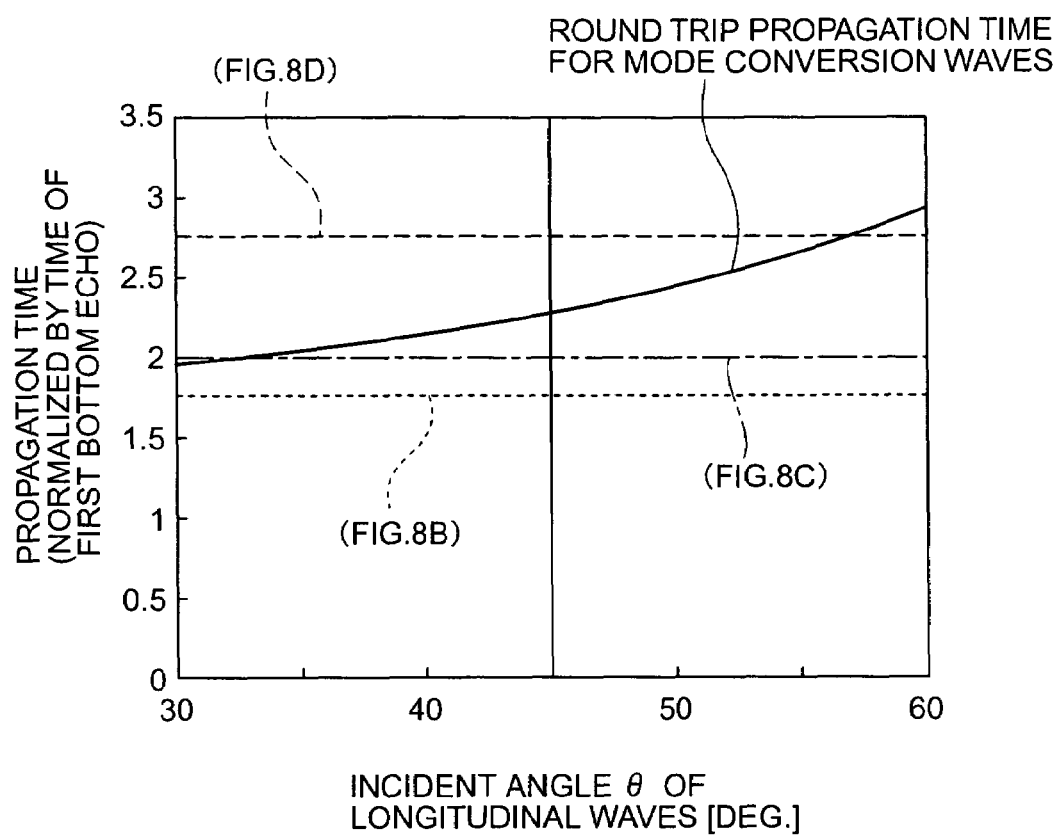
FIG. 15 is a graph explaining propagation times of echoes caused by mode conversion waves employed in the first embodiment of the present invention.

FIGS. 13, 14 and 15 are graphs comparing the total round-trip propagation time for mode conversion waves along the paths 501, 502 and 504 shown in FIGS. 5A and 5B with round-trip propagation times for multiple bottom echoes, in which FIGS. 13, 14 and 15 represent cases where the wave velocity ratio V/Vs is 2, 1.5, and 2.5, respectively. In the graphs, the longitudinal wave velocity V is fixed at 5900 m/s and the shear wave velocity Vs is changed depending on the wave velocity ratio V/Vs.

As is also clear from FIGS. 13, 14 and 15, in ordinary solid bodies having wave velocity ratios V/Vs within a range of 2±0.5, the round-trip propagation time for the mode conversion waves stays between the time corresponding to the sum of three times the wall thickness one-way propagation time for longitudinal waves and the wall thickness one-way propagation time for shear waves (FIG. 8D) and the time corresponding to the sum of the wall thickness one-way propagation time for longitudinal waves and the wall thickness one-way propagation time for shear waves (FIG. 8B) even if the flaw detection angle θ of the angled longitudinal wave technique deviates from 45° by approximately 5°.

Therefore, echoes caused by the mode conversion waves are displayed in the area 902 (which is surrounded by the two propagation times (FIG. 8B and FIG. 8D) and boundaries of the flaw detection angle (around 60°) for the mode conversion waves), and the approximate height of the defect can be judged based on the presence/absence of a signal in the area.

Figure 16A:
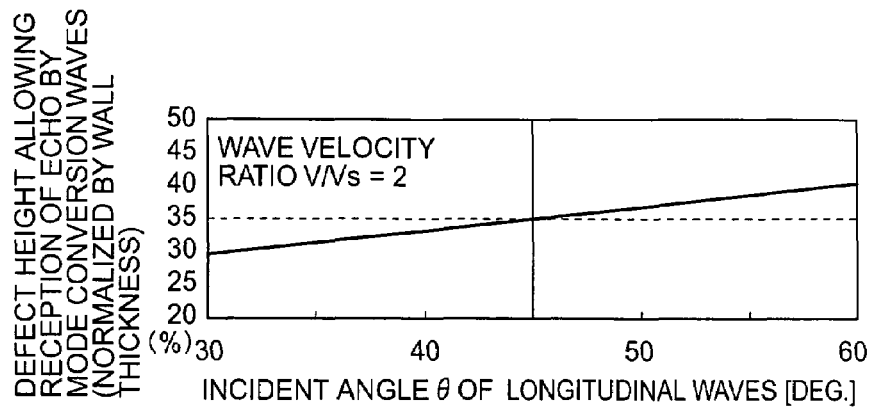
FIGS. 16A–16C are graphs showing defect heights allowing the reception of mode conversion waves in the first embodiment of the present invention.
Figure 16B:
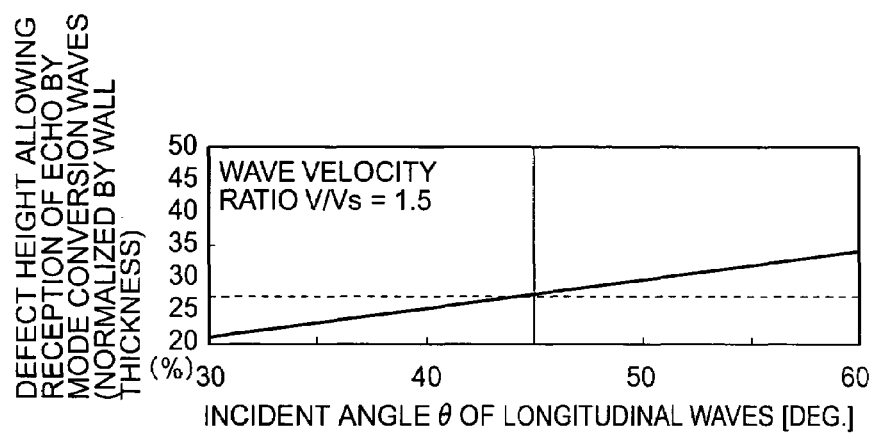
Figure 16C:
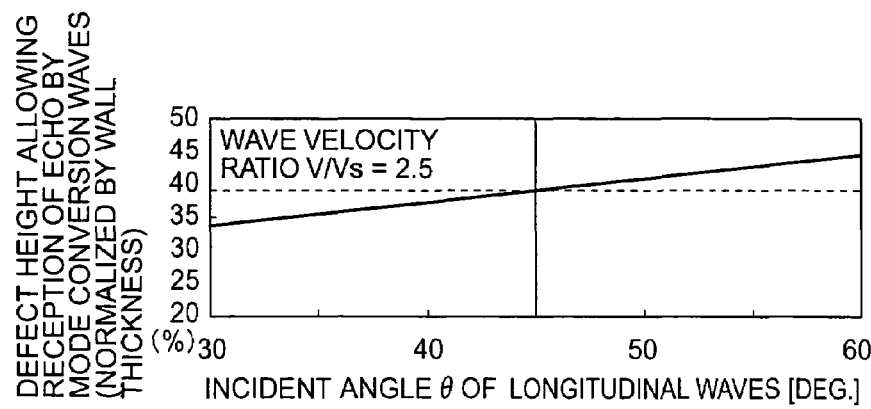

FIGS. 16A–16C are graphs showing defect heights allowing the reception of an echo caused by the mode conversion waves, in which FIGS. 16A, 16B and 16C represent cases where the wave velocity ratio V/Vs is 2, 1.5, and 2.5, respectively. In the graphs, the longitudinal wave velocity V is fixed at 5900 m/s and the shear wave velocity Vs is changed depending on the wave velocity ratio V/Vs. Although there exist slight differences among the three cases with different wave velocity ratios V/Vs (2±0.5), an echo caused by the mode conversion waves can be received when the height of the defect is approximately ⅓ of the wall thickness or more.

Next, a concrete example of a defect judgment method in accordance with the embodiment will be described with reference to FIGS. 25, 26, 27, 31 and 32. FIGS. 25, 26, 27, 31 and 32 are schematic diagrams showing examples of ultrasonic flaw detection result display screens. In the flaw detection regarding the figures, the array probe is assumed to be set on a specimen as shown in FIG. 1 and a probable crack (defect) in the specimen is assumed to be open to the far surface of the specimen.

Figure 25:
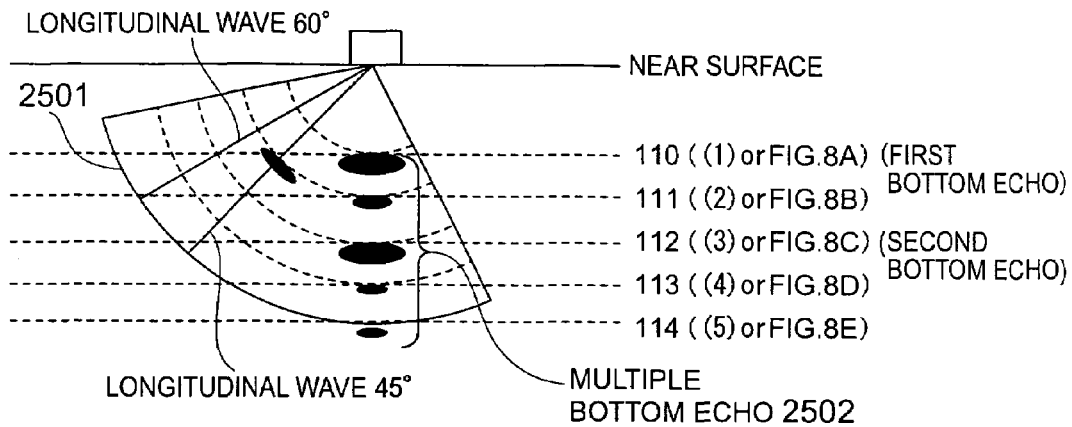
FIG. 25 is a schematic diagram showing an example of a flaw detection display screen when echoes caused by angled longitudinal waves are displayed in the first embodiment of the present invention.

On the display screen, the near surface of the specimen and a signal display area 2501 (in the shape of a fan corresponding to an incident angle range and a propagation time of ultrasonic waves) are displayed as shown in FIG. 25. For example, the incident angle range is set as a range between −5° and +85° and the propagation time is set at the time corresponding to the sum of the wall thickness round-trip propagation time for longitudinal waves and the wall thickness round-trip propagation time for shear waves.

In the signal display area 2501, signals which are received due to multiple echoes occurring between the near surface and the far surface of the specimen are displayed as multiple bottom echo signals 2502. In this case, the flaw detection results can be roughly classified into the following three groups.

Figure 27:
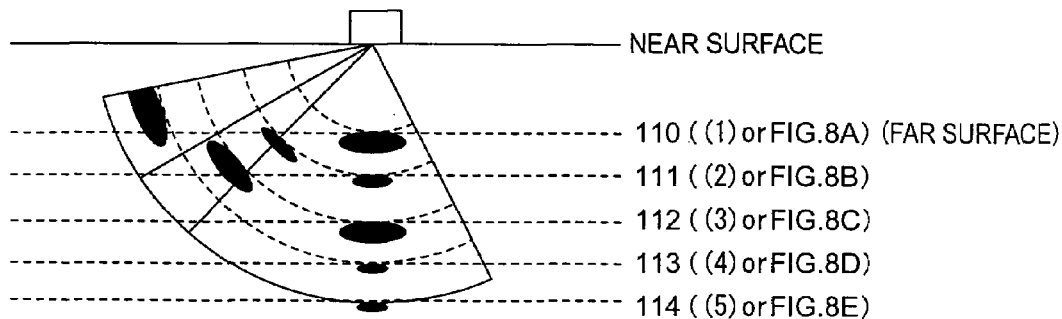
FIG. 27 is a schematic diagram showing an example of a flaw detection display screen when echoes caused by angled longitudinal waves, ID creeping waves and mode conversion waves are displayed in the first embodiment of the present invention.

The first is a case where an indication by the angled longitudinal wave technique (around 45°) is displayed in the are 901 (which has been explained referring to FIGS. 9A and 9B), an indication by the ID creeping waves is displayed in the are 903 (also explained referring to FIGS. 9A and 9B), and an indication by the mode conversion waves is displayed in the are 902 (also explained referring to FIGS. 9A and 9B) as shown in FIG. 27.

In this case, since indications are obtained by both the angled longitudinal waves and the ID creeping waves, the echoes from the part under consideration (where a defect might have occurred) are judged to have been caused by a defect. Since the mode conversion waves are also received, the height of the defect is judged to be ⅓ of the wall thickness or more and thus the defect is regarded as a relatively large crack.

Figure 26:
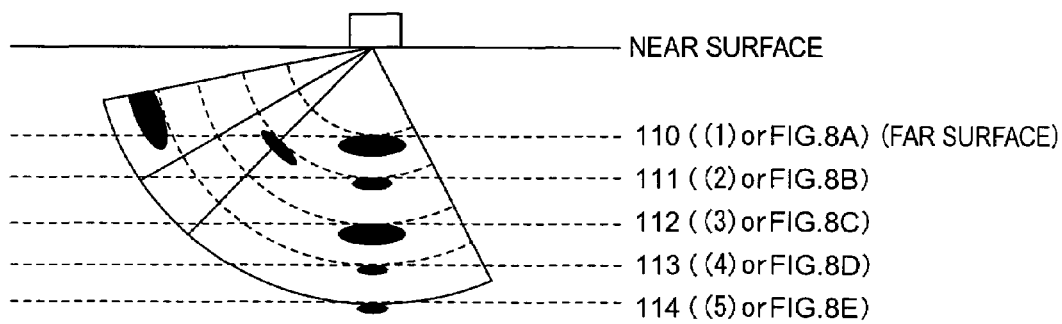
FIG. 26 is a schematic diagram showing an example of a flaw detection display screen when echoes caused by angled longitudinal waves and ID creeping waves are displayed in the first embodiment of the present invention.

The second is a case where indications are obtained in both the areas 901 and 903 (see FIGS. 9A and 9B) and no indication is obtained in the area 902 as shown in FIG. 26.

In this case, since both the angled longitudinal waves and the ID creeping waves provided indications, the indications are judged to have been caused by a defect.

However, the defect under consideration is judged to be a relatively small crack having a height less than ⅓ wall thickness since no echo deriving from the mode conversion waves is received in the area 902.

The third is a case where only an indication by the angled longitudinal waves is displayed in the area 901 (see FIGS. 9A and 9B) as shown in FIG. 25. In this case, since some kind of indication is obtained by the angled longitudinal waves, some type of reflector might be in the part under consideration (where a defect might have occurred); however, the reflector is judged not to be a defect.

Such reflectors other than defects include, for example, deformation or marks on the far surface of the specimen caused by welding or processing.

Figure 33:
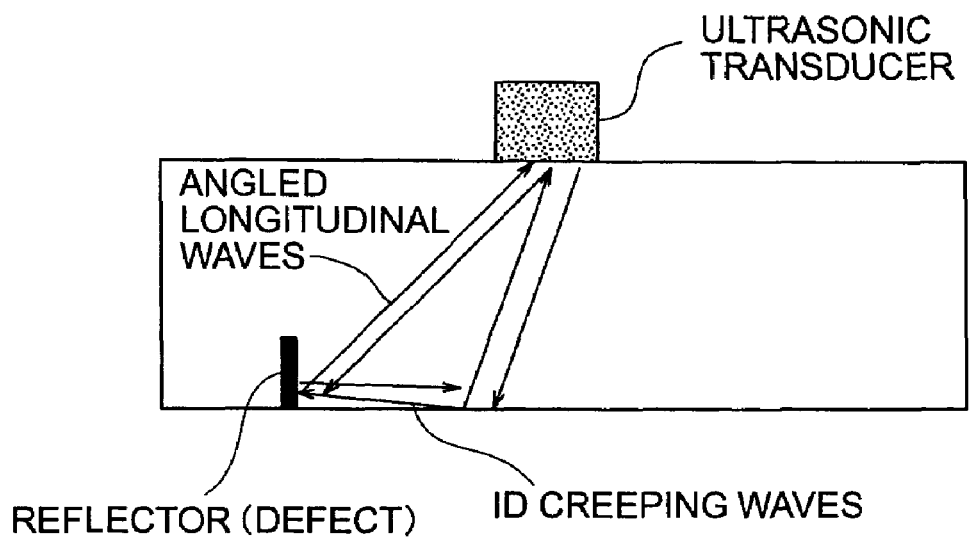
FIG. 33 is a schematic diagram explaining echoes occurring when there is a defect at a far surface of the specimen in the first embodiment of the present invention.

Here, examples of the condition of the far surface of the specimen in the above third case will be explained referring to FIGS. 33 and 34. When a defect exists at the far surface of the specimen as in the first and second cases, both the echoes deriving from the angled longitudinal waves and the ID creeping waves are obtained.

Figure 34:
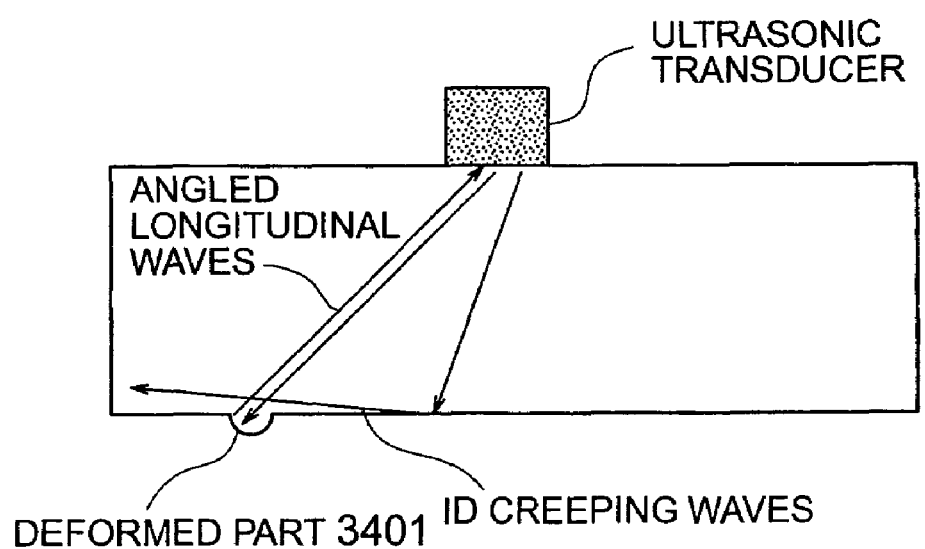
FIG. 34 is a schematic diagram explaining echoes occurring when there is a deformed part at the far surface of the specimen in the first embodiment of the present invention.

Meanwhile, when a deformed part like a penetration bead caused by welding exists on the far surface of the specimen as shown in FIG. 34, an indication by the angled longitudinal waves is received. However, the specimen has no crack-like reflector developing vertically from the far surface.

Therefore, no reflection occurs to the ID creeping waves at such a reflector (penetration bead caused by welding, etc.) other than a defect, by which no indication due to the ID creeping waves or mode conversion waves appears.

Figure 31:
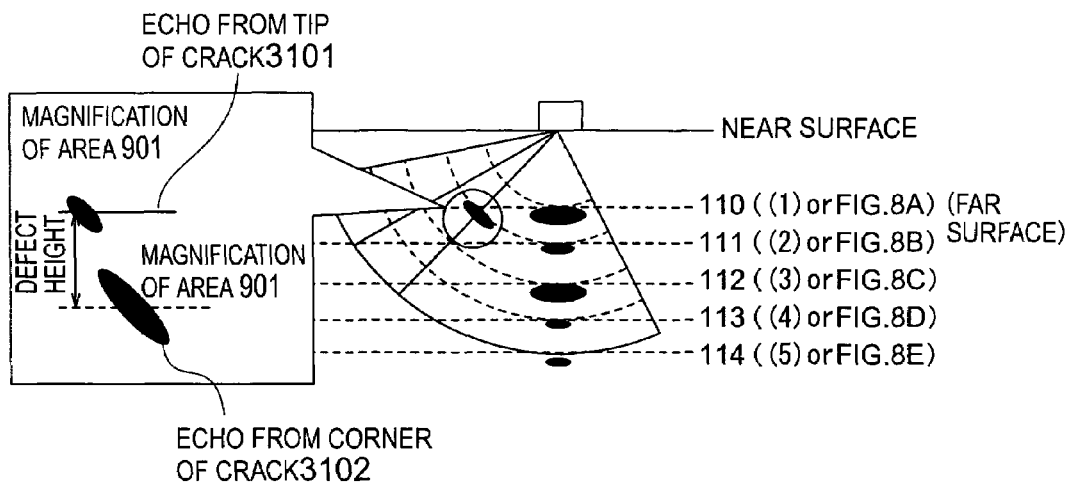
FIG. 31 is a schematic diagram explaining measurement of the height of a defect (crack) based on echoes from a tip and corner of the crack caused by angled longitudinal waves in the first embodiment of the present invention.

On the other hand, in the case where the specimen is judged to have a defect, the height of the defect (crack) may be estimated as shown in FIG. 31 based on the echoes displayed in the area 901 caused by the angled longitudinal waves (based on an echo 3102 from the tip of the crack and an echo 3101 from the corner of the crack).

Here, an example of the ultrasonic flaw detection result display screen according to the display method of this embodiment when an improper element pitch (different from the optimum element pitch in accordance with the embodiment of the present invention) is employed will be explained referring to FIG. 32.

Figure 32:
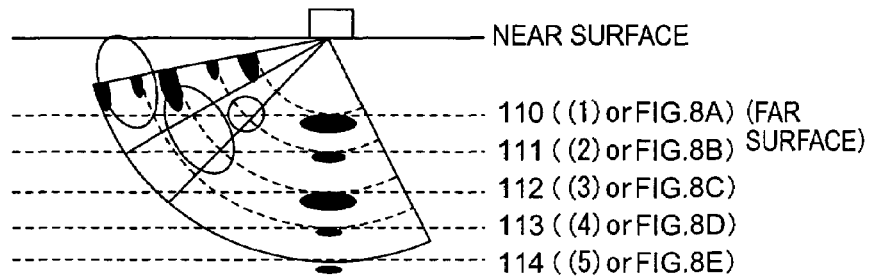
FIG. 32 is a schematic diagram showing an example of a flaw detection screen when an element pitch of the array probe is too large.

In this case without the proper element pitch enabling the transmission of the longitudinal waves and shear waves at intended angles, grating lobes develop in the specimen and thereby signals of multiple bottom echoes are displayed at parts of the screen corresponding to angles different from the intended angles, as shown in FIG. 32 for example.

The signals caused by the grating lobes (as noise on the screen) can hamper the judgment on the presence/absence of a signal in the areas 901, 902 and 903.

As described above, by the first embodiment of the present invention, an array probe having the optimum element pitch (achieving the transmission of main beams of both longitudinal waves and shear waves and the reduction of grating lobes) is employed, reception signals within the time corresponding to the sum of the wall thickness round-trip propagation time for longitudinal waves and the wall thickness round-trip propagation time for shear waves are displayed on the screen, and the five multiple bottom echoes (FIGS. 8A–8E) and the incident angles of the ultrasonic waves are especially taken into consideration of the reception signals, by which an ultrasonic flaw detection method and ultrasonic flaw detector having increased reliability, capable of realizing the ID creeping technique and the mode conversion technique in addition to the ordinary angled longitudinal wave technique even by use of an array probe, can be provided.

Incidentally, while the times of the multiple bottom echoes are directly obtained from multiple bottom echoes caused by the array probe that is used for the ultrasonic flaw detection in the examples of FIGS. 1, 8A–8F, etc., it is also possible in the embodiment of the present invention to measure times of multiple bottom echoes by use of a probe emitting ultrasonic waves in the vertical direction and use the measured times, for example.

Meanwhile, in cases where the longitudinal/shear wave velocities in the specimen and the wall thickness of the specimen are known, the times of multiple bottom echoes may also be obtained by calculation (by dividing the wall thickness by the longitudinal/shear wave velocity, etc.). In cases where the shear wave velocity in the specimen is unknown, half the longitudinal wave velocity may be used as a rough estimate of the shear wave velocity.

Embodiment 2

In the following, ultrasonic flaw detection suitable for cases where the specimen has a defect (crack) open to its near surface will be described as a second embodiment of the present invention. The array probe and the composition of the apparatus used for the flaw detection in the second embodiment is the same as those in the first embodiment.

Figure 17:
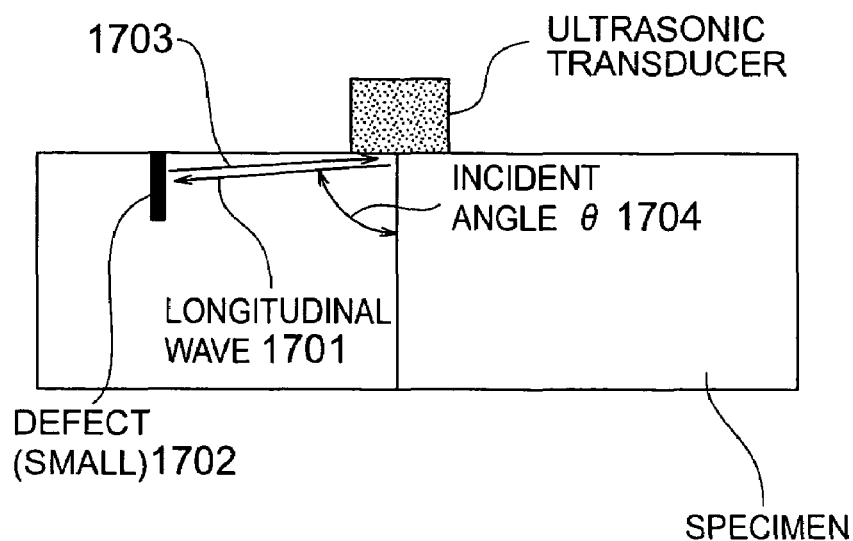
FIG. 17 is a schematic diagram explaining angled longitudinal wave flaw detection in search of a defect open to a near surface of the specimen.
Figure 18:
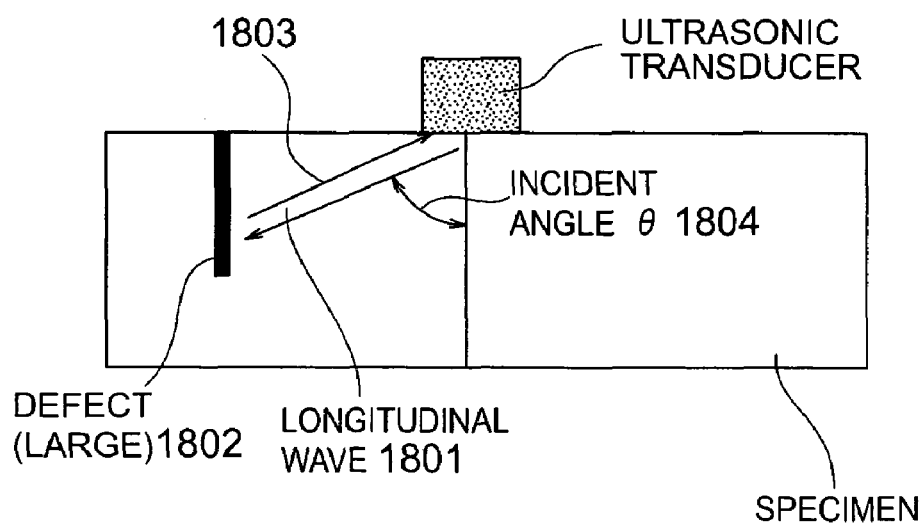
FIG. 18 is a schematic diagram explaining angled longitudinal wave flaw detection in search of a defect open to the near surface of the specimen.

Thus the following detailed explanation will be given mainly on the display of flaw detection results and the identification of waveforms. FIGS. 17 and 18 are schematic diagrams showing a brief outline of the propagation paths of ultrasonic waves in flaw detection by the angled longitudinal wave technique in search of a defect (crack) open to the near surface of the specimen, in which FIG. 17 shows a case where the defect height (depth) is relatively small and FIG. 18 shows a case where the defect height is relatively large.

In the case of FIG. 17 where the defect height is small, a longitudinal wave 1701 transmitted by the ultrasonic transducer is reflected in the vicinity of the corner of the crack 1702 (reflector), and a reflected longitudinal wave 1703 directly returns to the ultrasonic transducer and is received as a signal.

The longitudinal waves (1701, 1703) propagate in directions corresponding to incident angles 1704 between approximately 70° and 90°. Such longitudinal waves are called "OD creeping waves."

In the case of FIG. 18 where the defect height is large, a longitudinal wave 1801 transmitted by the ultrasonic transducer is reflected in the vicinity of the tip of the crack 1802 (reflector), and a reflected longitudinal wave 1803 returns to the ultrasonic transducer and is received as a signal. The incident angle 1804 of the longitudinal waves (1801, 1803) is around 60° (approximately between 45° and 70°).

Figure 19A:
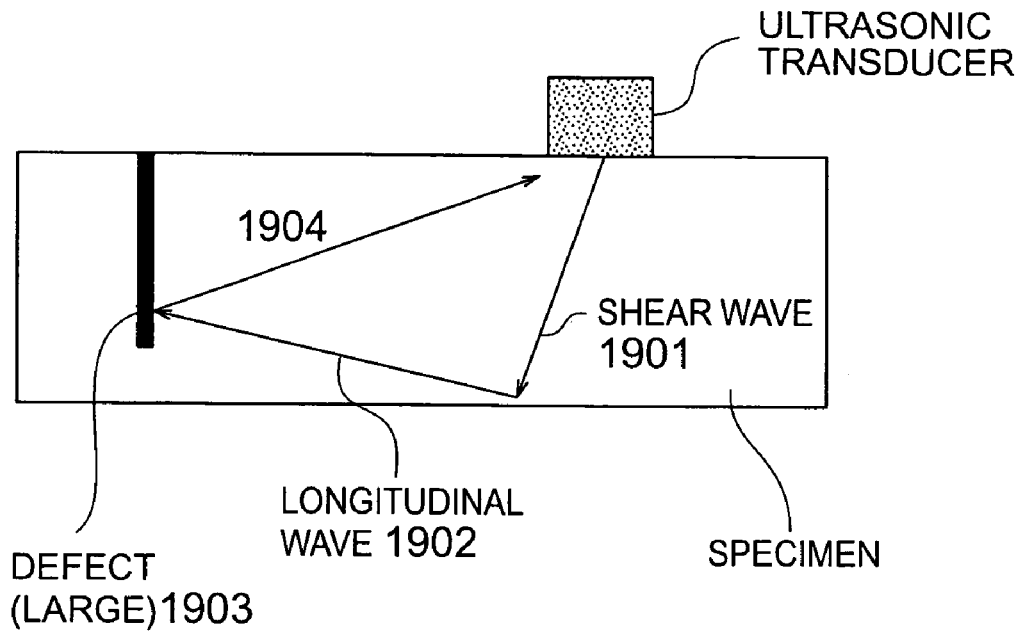
FIGS. 19A and 19B are schematic diagram explaining flaw detection by use of mode conversion waves in a second embodiment of the present invention.
Figure 19B:
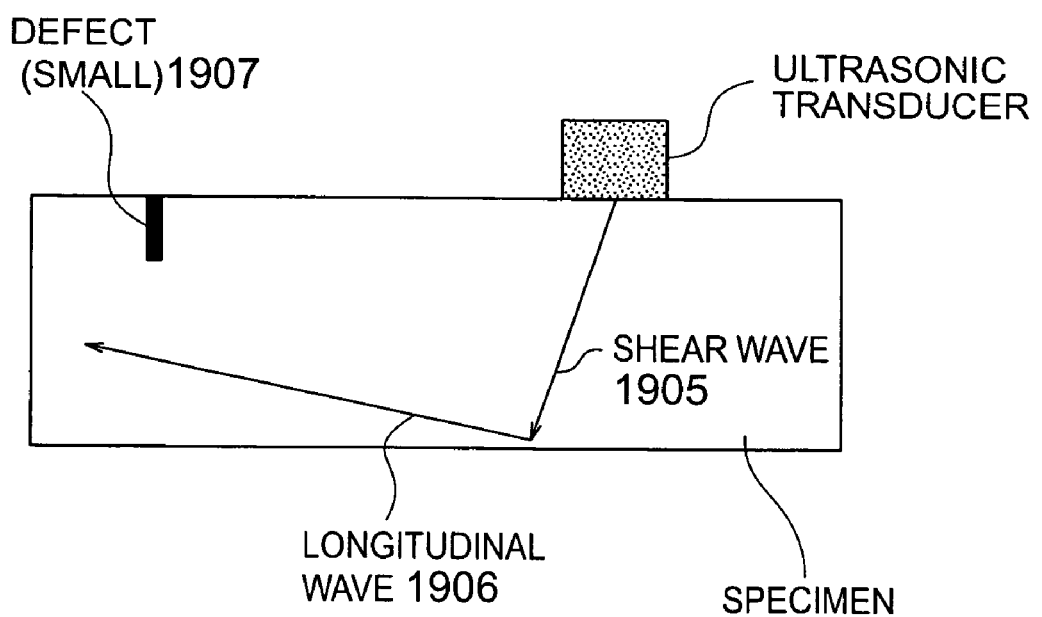

FIGS. 19A and 19B are schematic diagram showing a brief outline of the propagation paths of ultrasonic waves in flaw detection by the mode conversion technique in search of a defect (crack) open to the near surface of the specimen. Similarly to the case of FIGS. 5A and 5B (flaw detection in search of a crack open to the far surface of the specimen), the propagation mode of a shear wave 1901 generated by the ultrasonic transducer changes from the shear wave to a longitudinal wave 1902 when the wave is reflected by the far surface of the specimen.

When the reflector is a defect 1903 having a certain height (depth), the longitudinal wave 1902 reaches the tip of the defect or somewhere on the surface of the defect on the way to the tip as shown in FIG. 19A. A longitudinal wave 1904 reflected by the defect returns directly to the ultrasonic transducer through the specimen and is received as a reflected wave (echo) from the defect.

However, when the height of the reflector is relatively small like the defect 1907 shown in FIG. 19B, a longitudinal wave 1906 (generated by the mode conversion from a shear wave 1905 at the far surface of the specimen) can not meet the tip of the defect 1907, by which there occurs no ultrasonic wave returning to the ultrasonic transducer.

As above, in the flaw detection by the mode conversion technique in search of a defect open to the near surface of the specimen (mode conversion flaw detection from a surface that might have an open defect), whether the potential defect has a considerable height (approximately ⅔ of the wall thickness) or not can be evaluated.

Next, a concrete example of a waveform identification method in the case where the flaw detection is carried out in search of a defect open to the near surface of the specimen will be explained in detail referring to FIGS. 20A, 20B, 28, 29 and 30. When an echo that seems to be indicating a defect (hereinafter referred to as an "indication") is obtained, whether there exists a defect or not is judged according to the flow chart of FIG. 20B.

Figure 20A:
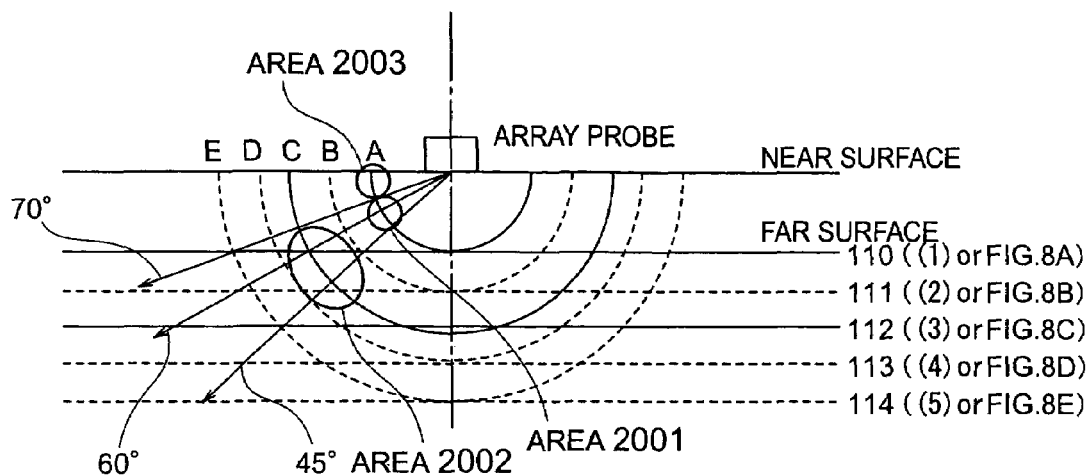
FIG. 20A is a schematic diagram showing a display method employed in the second embodiment of the present invention.
Figure 20B:
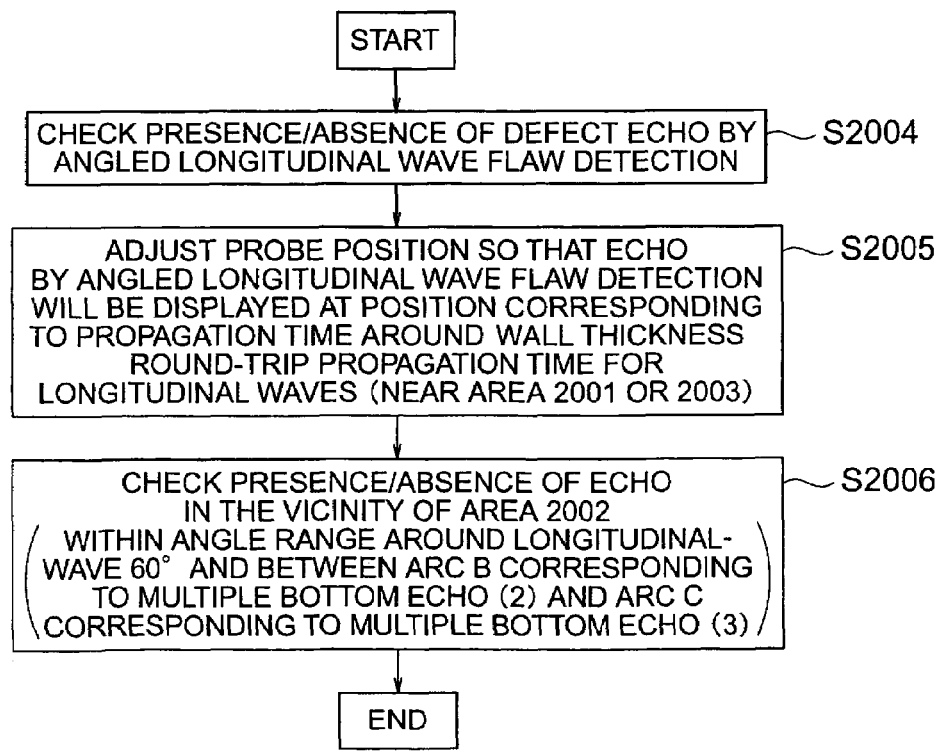
FIG. 20B is a flow chart showing a display method employed in the second embodiment of the present invention.

In the example of FIGS. 20A and 20B, the ultrasonic flaw detection is assumed to be carried out for a specimen having a crack (defect) open to its near surface. When an echo that seems to be indicating a defect (indication) is obtained, whether there exists a defect or not is judged for areas shown in FIG. 20A according to the flow chart of FIG. 20B.

First, the presence/absence of an indication is checked by an ordinary angled flaw detection technique (S2004). In this step, an echo that seems to have been reflected in the vicinity of the tip or the corner of a defect (crack) is detected depending on the height of the defect as explained above.

Subsequently, the position of the ultrasonic transducer is adjusted so that the indication that seems to be from the crack tip will be displayed in the vicinity of an area 2001 shown in FIG. 20A or so that the indication that seems to be from the crack corner will be displayed in the vicinity of an area 2003 shown in FIG. 20A (S2005).

Finally, the presence/absence of an echo in an area 2002 is checked in order to determine the presence/absence of an echo caused by a mode conversion wave (S2006). When a signal is found in the step S2004 or S2006, the indication is regarded to be one that might have been caused by a defect.

Here, before explaining a concrete example of flaw detection by use of the indications, characteristics of each area (2001, 2002, 2003) where a signal appears in each step of FIG. 20B will be explained.

Figure 21:
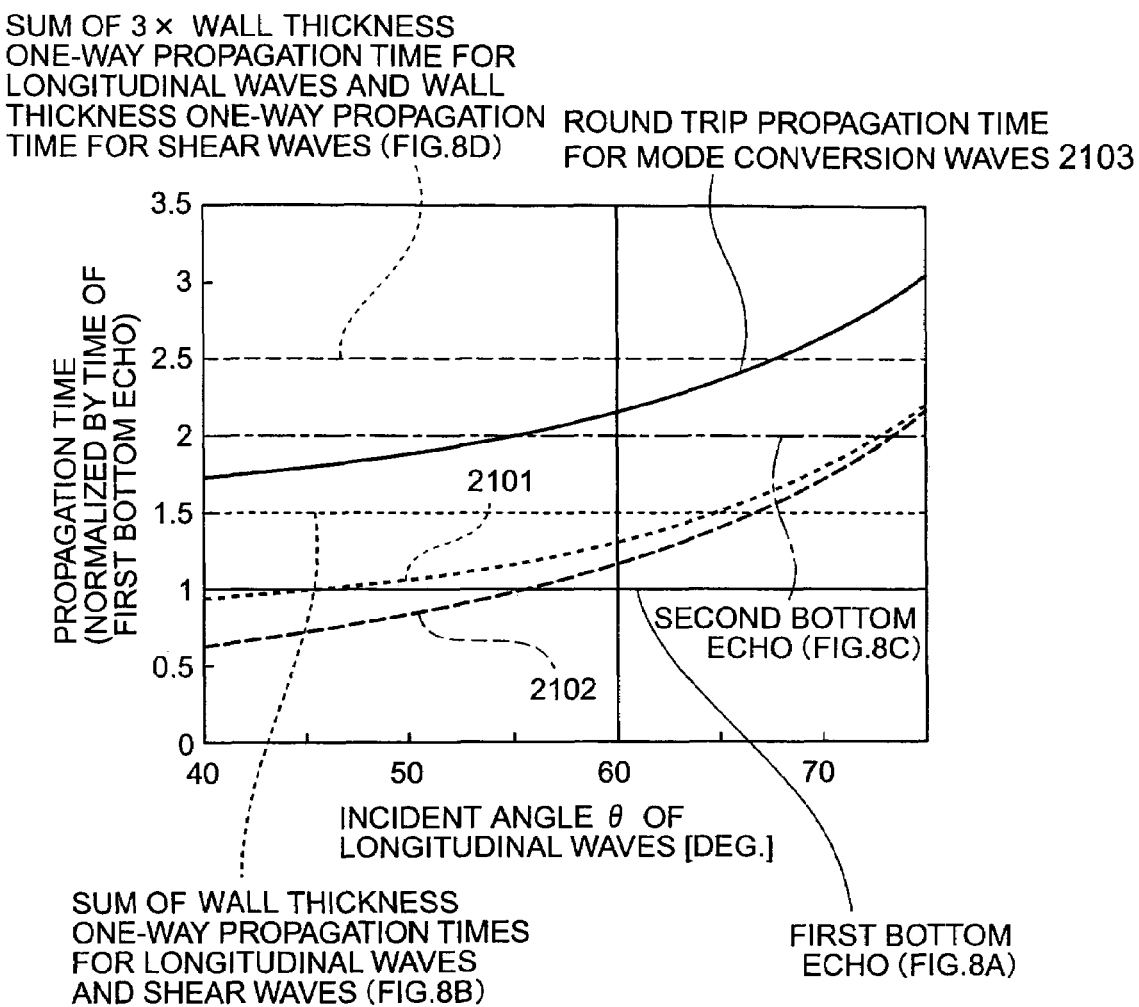
FIG. 21 is a graph explaining propagation times of echoes caused by mode conversion waves employed in the second embodiment of the present invention.
Figure 22:
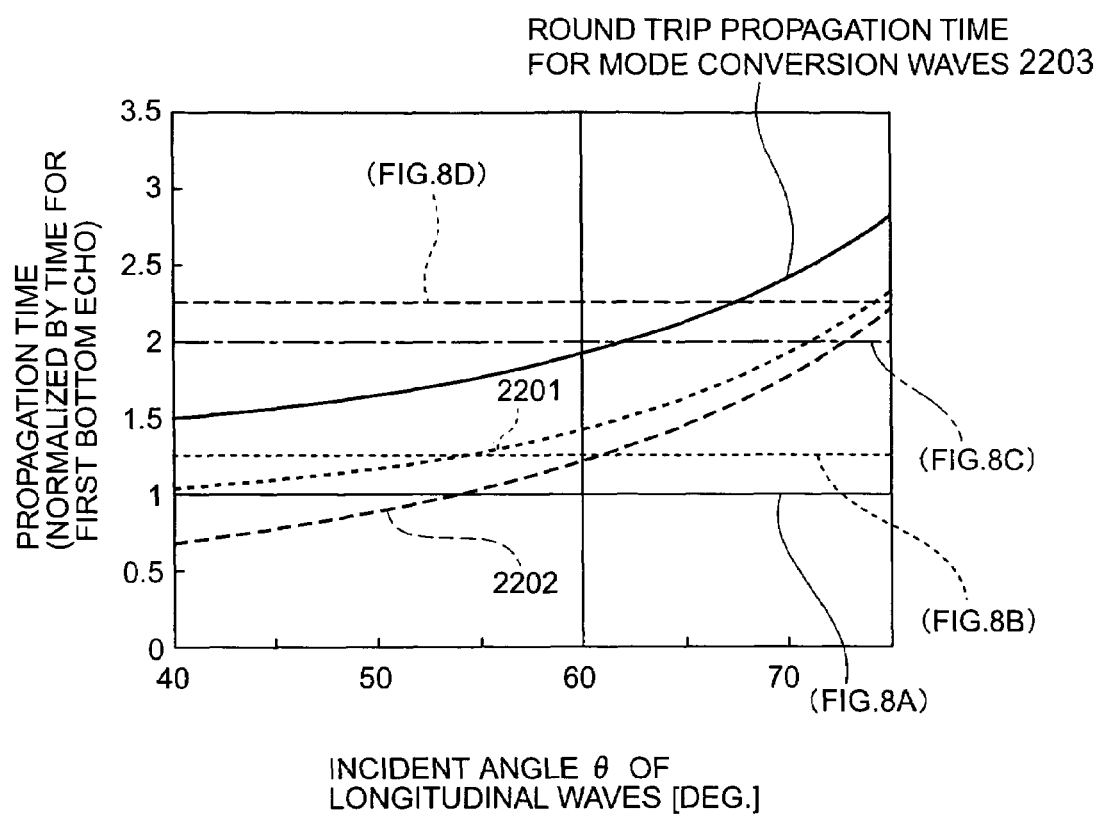
FIG. 22 is a graph explaining propagation times of echoes caused by mode conversion waves employed in the second embodiment of the present invention.
Figure 23:
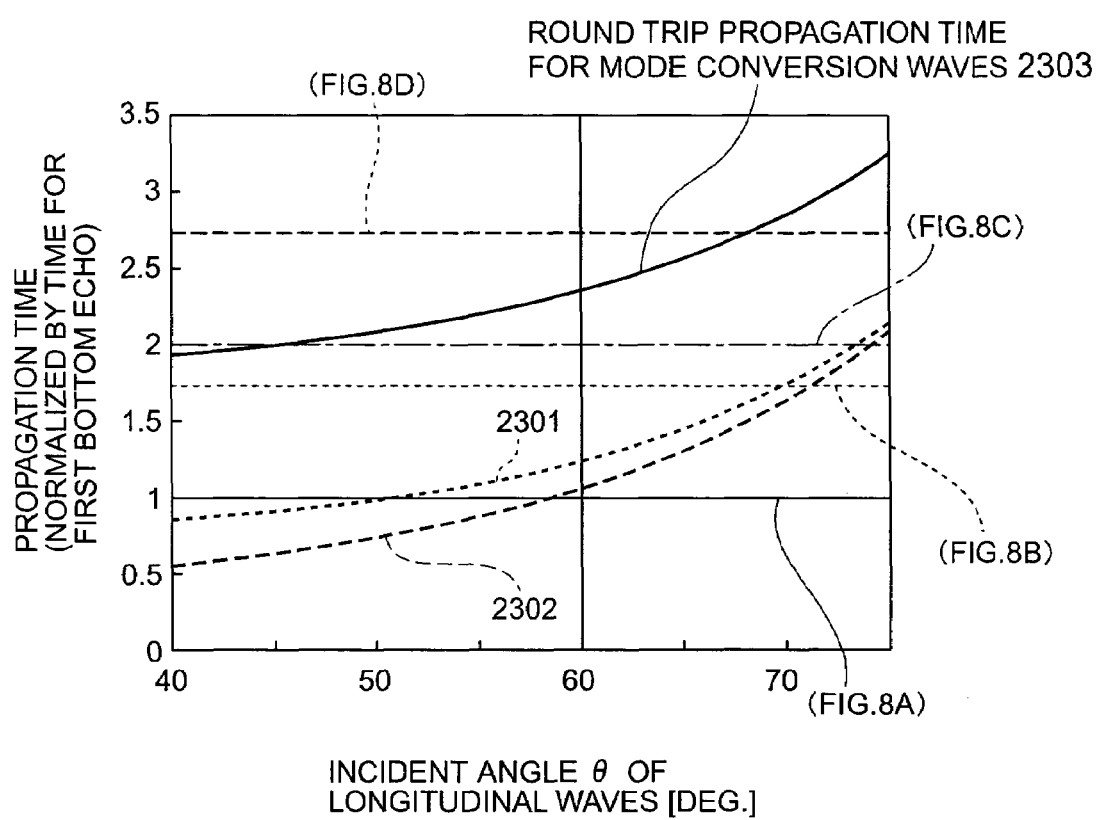
FIG. 23 is a graph explaining propagation times of echoes caused by mode conversion waves employed in the second embodiment of the present invention.

FIGS. 21–23 respectively show a sum of propagation times of echoes from a tip of crack in the angled longitudinal wave flaw detection method, that is a sum of paths of 1701 and 1703 in FIG. 17 and the propagation times of multiple bottom echoes, and a sum of propagation times of echoes from a surface of the crack corner in the OD creeping wave method, that is a sum of the paths of 1801 and 1803 in FIG. 18 and the propagation times of multiple bottom echoes, and a sum of propagation times of echoes in the mode conversion technique, that is a sum of paths of 1901, 1902, 1904 in FIG. 19A and the propagation times of multiple bottom echoes.

Incidentally, FIGS. 21, 22 and 23 represent cases where the wave velocity ratio V/Vs is 2, 1.5, and 2.5, respectively. In the graphs, the longitudinal wave velocity V is fixed at 5900 m/s and the shear wave velocity Vs is changed depending on the wave velocity ratio V/Vs.

<Area 2001>

As shown in FIGS. 21, 22 and 23, in angled flaw detection in search of a defect from a defect opening surface side of the specimen (ordinary solid body having a wave velocity ratio V/Vs within a range of 2±0.5), the propagation time (2101, 2201, 2301) of the echo from the crack tip which has propagation paths of FIG. 18 and the propagation time (2102, 2202, 2302) of the echo from the crack corner which has propagation paths of FIG. 17 deriving from the OD creeping waves (longitudinal waves 70°–90°) take a similar propagation time to that of the first bottom echo (FIG. 8A) in the specimen.

Especially, the relationship is satisfied also in the case of 60° longitudinal waves (which is important among the mode conversion waves) as seen in FIGS. 21, 22 and 23. Thus, out of the echoes obtained by the angled longitudinal wave technique, the echo from the crack corner caused by the OD creeping waves is displayed in the vicinity of the area 2003 (where the wall thickness round-trip propagation time for longitudinal waves (FIG. 8A) overlaps with an angle range approximately between refraction angles 70° and 90°), and the echo from the crack tip caused by the angled longitudinal waves is displayed in the vicinity of the area 2001 (where the wall thickness round-trip propagation time (FIG. 8A) overlaps with an angle range around a refraction angle 60°).

<Area 2002>

In the judgment on the presence/absence of a defect by use of mode conversion waves, it is assumed that an indication by the angled longitudinal wave flaw detection has already been displayed in the area 2001 or in the vicinity of the area 2001.

As is clear from FIGS. 21, 22 and 23, in ordinary solid bodies having wave velocity ratios V/Vs within a range of 2±0.5, the round-trip propagation time for the mode conversion waves (2103, 2203, 2303) stays between the time corresponding to the sum of three times the wall thickness one-way propagation time for longitudinal waves and the wall thickness one-way propagation time for shear waves (FIG. 8D) and the time corresponding to the sum of the wall thickness one-way propagation time for longitudinal waves and the wall thickness one-way propagation time for shear waves (FIG. 8B) even if the flaw detection angle of the angled longitudinal wave technique for receiving an echo from a crack tip deviates from 60° by approximately 5°.

Therefore, echoes caused by the mode conversion waves are displayed in the area 2002 (which is surrounded by the two propagation times (FIG. 8B and FIG. 8D) and boundaries of the flaw detection angle (around 60°) for the mode conversion waves), and the approximate height of the defect can be judged based on the presence/absence of a signal in the area.

Figure 24A:
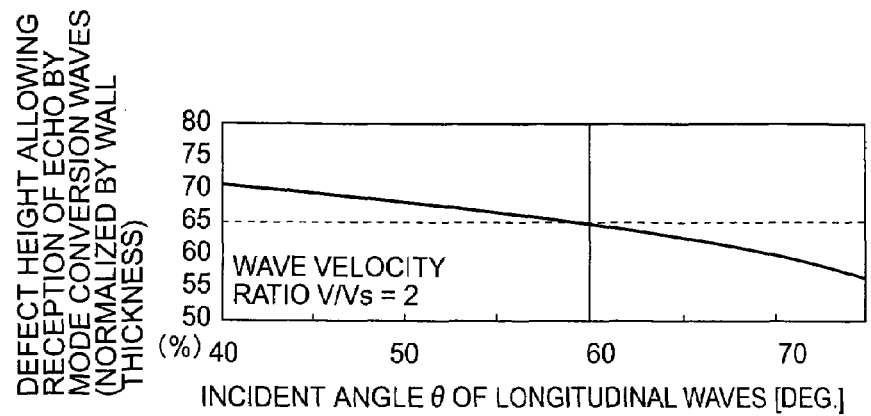
FIGS. 24A–24C are graphs showing defect heights allowing the reception of mode conversion waves in the second embodiment of the present invention.
Figure 24B:
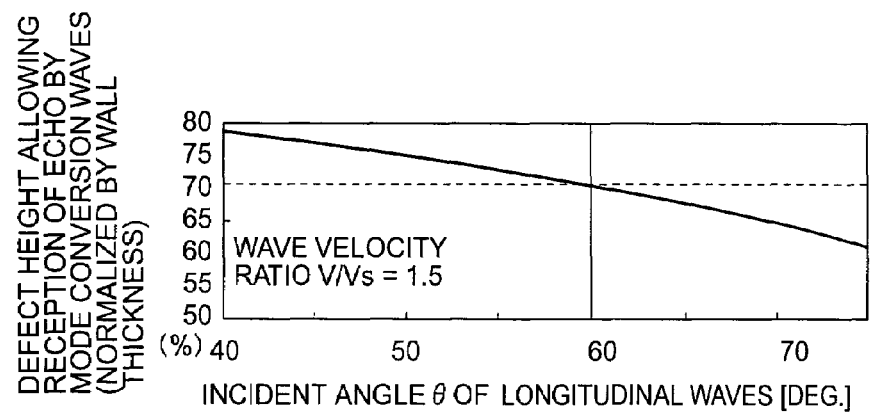
Figure 24C:
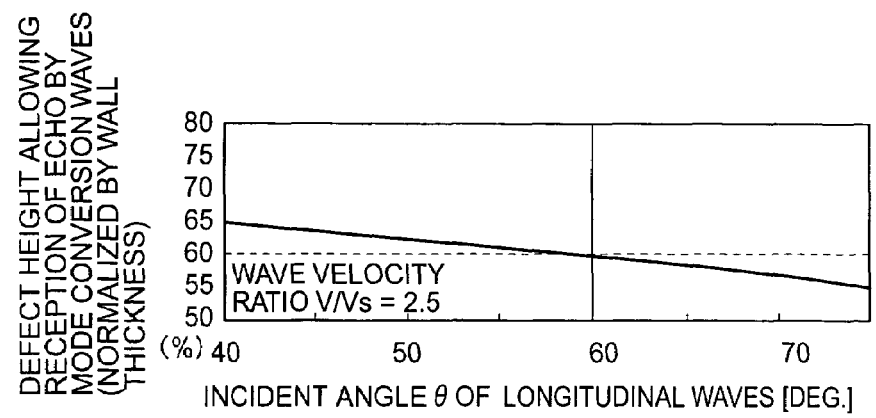

FIGS. 24A–24C are graphs showing defect heights allowing the reception of an echo caused by the mode conversion waves, in which FIGS. 24A, 24B and 24C represent cases where the wave velocity ratio V/Vs is 2, 1.5, and 2.5, respectively. In the graphs, the longitudinal wave velocity V is fixed at 5900 m/s and the shear wave velocity Vs is changed depending on the wave velocity ratio V/Vs. Although there exist slight differences among the three cases with different wave velocity ratios V/Vs (2±0.5), an echo caused by the mode conversion waves can be received when the height of the defect is approximately ⅔ of the wall thickness or more.

Figure 28:
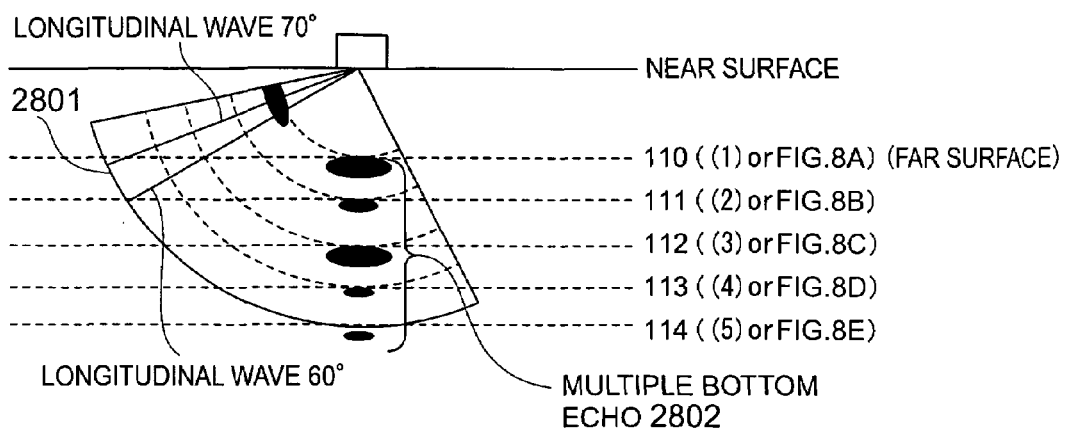
FIG. 28 is a schematic diagram showing an example of a flaw detection display screen when an echo from a part of the specimen in the vicinity of a crack corner caused by angled longitudinal waves is displayed in the second embodiment of the present invention.
Figure 29:
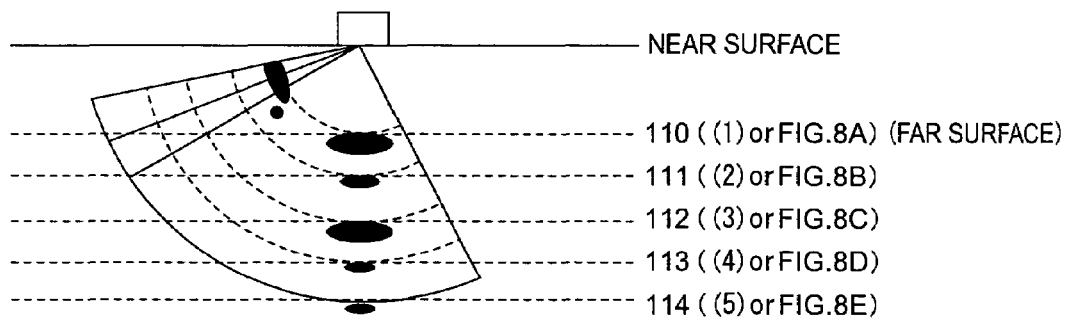
FIG. 29 is a schematic diagram showing an example of a flaw detection display screen when echoes from parts of the specimen in the vicinity of a crack corner and a crack tip caused by angled longitudinal waves are displayed in the second embodiment of the present invention.
Figure 30:
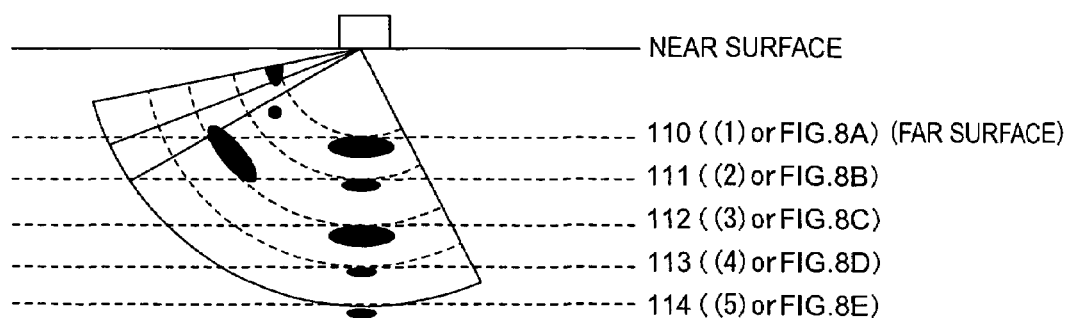
FIG. 30 is a schematic diagram showing an example of a flaw detection display screen when echoes from parts of the specimen in the vicinity of a crack corner and a crack tip caused by angled longitudinal waves and echoes caused by mode conversion waves are displayed in the second embodiment of the present invention.

Next, a concrete example of a defect judgment method in accordance with the embodiment will be described with reference to FIGS. 28, 29 and 30. FIGS. 28, 29 and 30 are schematic diagrams showing examples of ultrasonic flaw detection result display screens.

The flaw detection regarding the figures is assumed to be carried out by setting the array sensor (probe) explained referring to FIG. 1 on a specimen, and a probable crack (defect) in the specimen is assumed to be open to the near surface of the specimen.

On the display screen, the near surface of the specimen and a signal display area 2801 (in the shape of a fan corresponding to an incident angle range and a propagation time of ultrasonic waves) are displayed as shown in FIG. 28.

For example, the incident angle range is set as a range between −5° and +85° and the propagation time is set at the time corresponding to the sum of the wall thickness round-trip propagation time for longitudinal waves and the wall thickness round-trip propagation time for shear waves.

In the signal display area 2801, signals which are received due to multiple echoes occurring between the near surface and the far surface of the specimen are displayed as multiple bottom echo signals 2802. In this case, the flaw detection results can be roughly classified into the following three groups.

The first is a case where an indication by the angled longitudinal wave technique (approximately 70°–90°) that seems to be from a part of the specimen in the vicinity of a crack corner is displayed in the area 2003, an indication by the angled longitudinal wave technique that seems to be from a part of the specimen in the vicinity of a crack tip is displayed in the area 2001, and an indication by the mode conversion waves is displayed in the area 2002 as shown in FIG. 30.

In this case, since the indication that appears to be from the crack corner part is obtained by the angled longitudinal wave technique, the echoes from the part under consideration (where a defect might have occurred) are judged to have been caused by a defect. Since the indication by the mode conversion waves are also received, the defect is judged to be a considerably large crack having a height (depth from the near surface) of approximately ⅔ wall thickness or more.

At this stage, if a defect depth estimated from the indication by the angled longitudinal wave technique that seems to be from the crack tip part coincides with the estimate (⅔ wall thickness or more) by the mode conversion waves, the defect height (depth) is evaluated based on the echo from the crack tip part obtained by the angled longitudinal wave technique.

If the two estimates do not coincide with each other, the echo that seems to be from the crack tip part might not have captured the crack tip and thus an extra detailed flaw detection becomes necessary.

The second is a case where indications are obtained in both the areas 2001 and 2003 and no indication is obtained in the area 2002 as shown in FIG. 29.

In this case, since the indication that appears to be from the crack corner part is obtained by the angled longitudinal wave technique, the indications are judged to have been caused by a defect. However, the defect under consideration is judged to be a relatively small crack having a height less than ⅔ wall thickness since no echo deriving from the mode conversion waves is received in the area 2002.

At this stage, if a defect depth estimated from the indication by the angled Longitudinal wave technique that seems to be from the crack tip part coincides with the estimate (less than ⅔ wall thickness) by the mode conversion waves, the defect height (depth) is evaluated based on the echo from the crack tip part obtained by the angled longitudinal wave technique.

If the two estimates do not coincide with each other, the echo that seems to be from the crack tip part might not have captured the crack tip and thus an extra detailed flaw detection becomes necessary.

The third is a case where only an indication by the angled longitudinal waves is displayed in the area 2001 as shown in FIG. 28.

In the case of flaw detection in search of a defect open to the near surface of the specimen (flaw detection from a surface that might have an open defect), it is possible in many cases to determine the position of a crack corner by techniques other than the ultrasonic flaw detection (e.g. liquid penetrant flaw detection, eddy current flaw detection, visual inspection by the unaided eye or by a camera).

If the defect position by another technique coincides with that by the ultrasonic flaw detection, the indication displayed in the area 2001 can be regarded as an echo from a part of the specimen in the vicinity of a crack corner.

On the other hand, if the defect position obtained by the ultrasonic flaw detection contradicts that by another technique, the indication displayed in the area 2001 may not be an echo from a crack corner part and thus an extra flaw detection becomes necessary. In the former case where the defect position by the ultrasonic flaw detection coincides with that by another technique, the defect is judged to be a relatively small crack having a height less than ⅓ wall thickness since no echo by the angled longitudinal wave technique from a crack tip part nor echo by the mode conversion waves is received.

If possible, it is desirable that the comparison between the echo displayed in the area 2001 and the defect position obtained by another technique (explained above for the third case) should be made also for the first and second cases in order to confirm that there is no contradiction between the results.

In the case where the specimen is judged to have a defect, the height of the defect (crack) can be estimated by a method similar to that explained referring to FIG. 31.

Also in the second embodiment in search of a defect open to the near surface of the specimen, if an array probe having an element pitch different from the optimum element pitch most suitable for the reduction of grating lobes is used, the judgment on the presence/absence of signals in the areas 2001, 2002 and 2003 might be hampered similarly to the case in the first embodiment.

As described above, by the second embodiment of the present invention, also in the flaw detection in search of a defect open to the near surface of the specimen (flaw detection from a surface that might have an open defect), an array probe having the optimum element pitch reducing grating lobes and capable of transmitting main beams of both longitudinal waves and shear waves is employed, reception signals within the time corresponding to the sum of the wall thickness round-trip propagation time for longitudinal waves and the wall thickness round-trip propagation time for shear waves are displayed on the screen, and the five multiple bottom echoes (FIGS. 8A–8E) and the incident angles of the ultrasonic waves are especially taken into consideration of the reception signals, by which an ultrasonic flaw detection method and ultrasonic flaw detector having increased reliability, capable of realizing the mode conversion technique in addition to the ordinary angled longitudinal wave technique even by use of an array probe, can be provided.

Incidentally, as for the times of the multiple bottom echoes shown in FIGS. 1, 20A, 20B, etc., instead of directly obtaining the times from multiple bottom echoes caused by the array probe that is used for the ultrasonic flaw detection as above, it is also possible to measure times of multiple bottom echoes by use of an extra probe emitting ultrasonic waves in the vertical direction and use the measured times.

Meanwhile, in cases where the longitudinal/shear wave velocities in the specimen and the wall thickness of the specimen are known, the times of multiple bottom echoes may also be obtained by calculation (by dividing the wall thickness by the longitudinal/shear wave velocity, etc.).

In cases where the shear wave velocity in the specimen is unknown, half the longitudinal wave velocity may be used as a rough estimate of the shear wave velocity.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

The invention claimed is:

1. An ultrasonic flaw detection method according to a phased array technique employing an array probe including an array of transducer elements, wherein;
 a distance between centers of adjacent transducer elements in the array probe is set longer than ¼ of a wavelength of longitudinal waves in a specimen as the object of flaw detection and shorter than ½ of the wavelength; and
 reception signals obtained by the array probe are displayed for a period covering at least a time corresponding to the sum of round-trip propagation time for longitudinal waves in a wall thickness direction of the specimen and round-trip propagation time for shear waves in the wall thickness direction.

2. The ultrasonic flaw detection method according to claim 1, wherein integrity of the specimen is evaluated based on presence/absence of a signal displayed after time corresponding to twice the round-trip propagation time for longitudinal waves in the wall thickness direction and before time corresponding to the sum of the round-trip propagation time for longitudinal waves in the wall thickness direction and the round-trip propagation time for shear waves in the wall thickness direction.

3. The ultrasonic flaw detection method according to claim 1, wherein integrity of the specimen is evaluated based on presence/absence of a signal displayed after time corresponding to the sum of one-way propagation time for longitudinal waves in the wall thickness direction of the specimen and one-way propagation time for shear waves in the wall thickness direction and before time corresponding to the sum of three times the one-way propagation time for longitudinal waves in the wall thickness direction and the one-way propagation time for shear waves in the wall thickness direction.

4. An ultrasonic flaw detector employing an array probe including an array of transducer elements and operating according to a phased array technique,
 wherein a distance between centers of adjacent transducer elements in the array probe is set longer than ¼ of a wavelength of longitudinal waves in a specimen as the object of flaw detection and shorter than ½ of the wavelength; and
 wherein said ultrasonic flow detector further comprises a display system which displays reception signals obtained by the array probe for a period covering at least a time corresponding to the sum of round-trip propagation time for longitudinal waves in a wall thickness direction of the specimen and round-trip propagation time for shear waves in the wall thickness direction.

5. The ultrasonic flaw detector according to claim 4, further comprising a display system which displays reception signals obtained by the array probe after time corresponding to twice the round-trip propagation time for longitudinal waves in the wall thickness direction and before time corresponding to the sum of the round-trip propagation time for longitudinal waves in the wall thickness direction and the round-trip propagation time for shear waves in the wall thickness direction.

6. The ultrasonic flaw detector according to claim 4, further comprising a display system which displays reception signals obtained by the array probe after time corresponding to the sum of one-way propagation time for longitudinal waves in the wall thickness direction of the specimen and one-way propagation time for shear waves in the wall thickness direction and before time corresponding to the sum of three times the one-way propagation time for longitudinal waves in the wall thickness direction and the one-way propagation time for shear waves in the wall thickness direction.

* * * * *